United States Patent
Goodman et al.

(10) Patent No.: US 8,999,273 B2
(45) Date of Patent: Apr. 7, 2015

(54) METHODS AND DEVICES FOR PREPARING MICROSCOPY SAMPLES

(75) Inventors: Steven L. Goodman, Madison, WI (US);
Mark T. Nelson, Marshfield, WI (US);
Jack C. LaSee, Abbotsford, WI (US)

(73) Assignee: Microscopy Innovations, LLC, Marshfield, WI (US)

( * ) Notice: Subject to any disclaimer, the term of this patent is extended or adjusted under 35 U.S.C. 154(b) by 225 days.

(21) Appl. No.: 13/196,795

(22) Filed: Aug. 2, 2011

(65) Prior Publication Data

US 2012/0027650 A1   Feb. 2, 2012

Related U.S. Application Data

(60) Provisional application No. 61/369,931, filed on Aug. 2, 2010.

(51) Int. Cl.
| | | |
|---|---|---|
| *B01L 9/00* | (2006.01) | |
| *G02B 21/26* | (2006.01) | |
| *H01J 37/20* | (2006.01) | |
| *G01N 35/10* | (2006.01) | |

(52) U.S. Cl.
CPC ........ *G02B 21/26* (2013.01); *G01N 2035/1053* (2013.01); *H01J 37/20* (2013.01)

(58) Field of Classification Search
CPC .............................................. G01N 2035/1053
USPC ............... 422/561, 560, 549, 558; 206/316.1
See application file for complete search history.

(56) References Cited

U.S. PATENT DOCUMENTS

| | | |
|---|---|---|
| 2,783,180 A | 2/1957 | Whitehead |
| 4,363,783 A | 12/1982 | Sitte |
| 5,080,869 A | 1/1992 | McCormick |

(Continued)

FOREIGN PATENT DOCUMENTS

| | | |
|---|---|---|
| EP | 2041543 | 4/2009 |
| WO | 03019148 | 3/2003 |

(Continued)

OTHER PUBLICATIONS

International Preliminary Report on Patentability and Written Opinion; International Application No. PCT/US2011/046328; International Filing Date Aug. 2, 2011; Date of Mailing Feb. 14, 2013; 8 pages.

(Continued)

*Primary Examiner* — Natalia Levkovich
(74) *Attorney, Agent, or Firm* — Cantor Colburn LLP

(57) ABSTRACT

A system for preparing and holding specimens for microscopic analysis including a capsule having an open end, an opposite end including at least one aperture and a reservoir. The system also includes an insert with a base including at least one aperture. The insert fits within and engages an inner wall of the reservoir to secure the insert within the reservoir. The system also includes an insertion tool configured to engage the insert. The insertion tool is sized to position the insert within the reservoir at a variety of positions within the reservoir. The insertion tool will disengage the insert once the insert is positioned within the reservoir. A method of positioning a specimen within a capsule for processing the specimen in preparation for microscopic analysis. A tray for holding a plurality of pipette tips in such a way that a lower end of each pipette tip is sealed.

13 Claims, 16 Drawing Sheets

(56) References Cited

U.S. PATENT DOCUMENTS

| | | |
|---|---|---|
| 5,139,031 A | 8/1992 | Guirguis |
| 5,543,114 A | 8/1996 | Dudek |
| 5,556,598 A * | 9/1996 | Raybuck et al. ............. 422/525 |
| 5,686,313 A | 11/1997 | Sitte |
| 5,821,115 A | 10/1998 | Graupner |
| 5,837,198 A | 11/1998 | Itani |
| 6,017,476 A | 1/2000 | Renshaw |
| 6,157,446 A | 12/2000 | Baer et al. |
| 6,395,234 B1 | 5/2002 | Hunnell et al. |
| 7,005,110 B2 | 2/2006 | Taft et al. |
| 7,083,761 B2 | 8/2006 | Zimmermann et al. |
| 7,122,155 B2 | 10/2006 | Waterbury et al. |
| 7,179,424 B2 | 2/2007 | Williamson et al. |
| 7,544,953 B2 | 6/2009 | Goodman |
| 7,663,101 B2 | 2/2010 | Goodman |
| 2004/0248237 A1 | 12/2004 | Petit |
| 2008/0068706 A1 * | 3/2008 | Goodman ..................... 359/368 |

FOREIGN PATENT DOCUMENTS

| | | |
|---|---|---|
| WO | 2004041994 | 5/2004 |
| WO | 2006012486 | 2/2006 |
| WO | WO2007137272 | 11/2007 |

OTHER PUBLICATIONS

International Search Report and Written Opinion; International Application No. PCT/US2011/046328; International Filing Date Aug. 2, 2011; Date of Mailing Mar. 21, 2012; 10 pages.

* cited by examiner

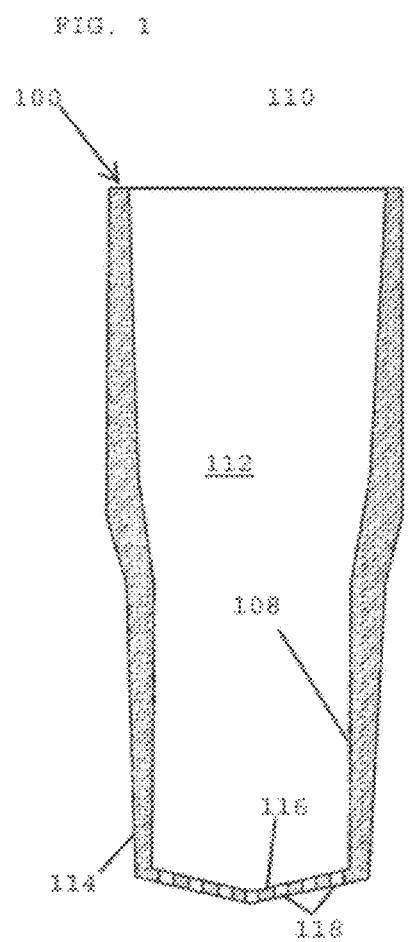
FIG. 1
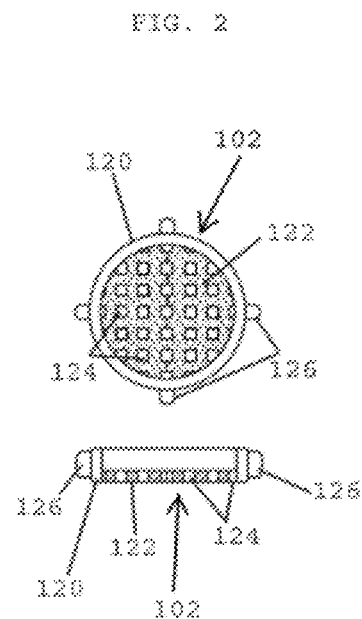
FIG. 2
FIG. 3
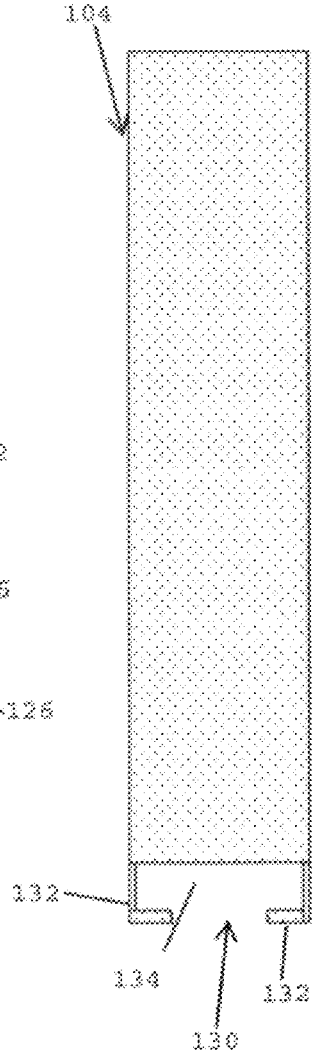
FIG. 4

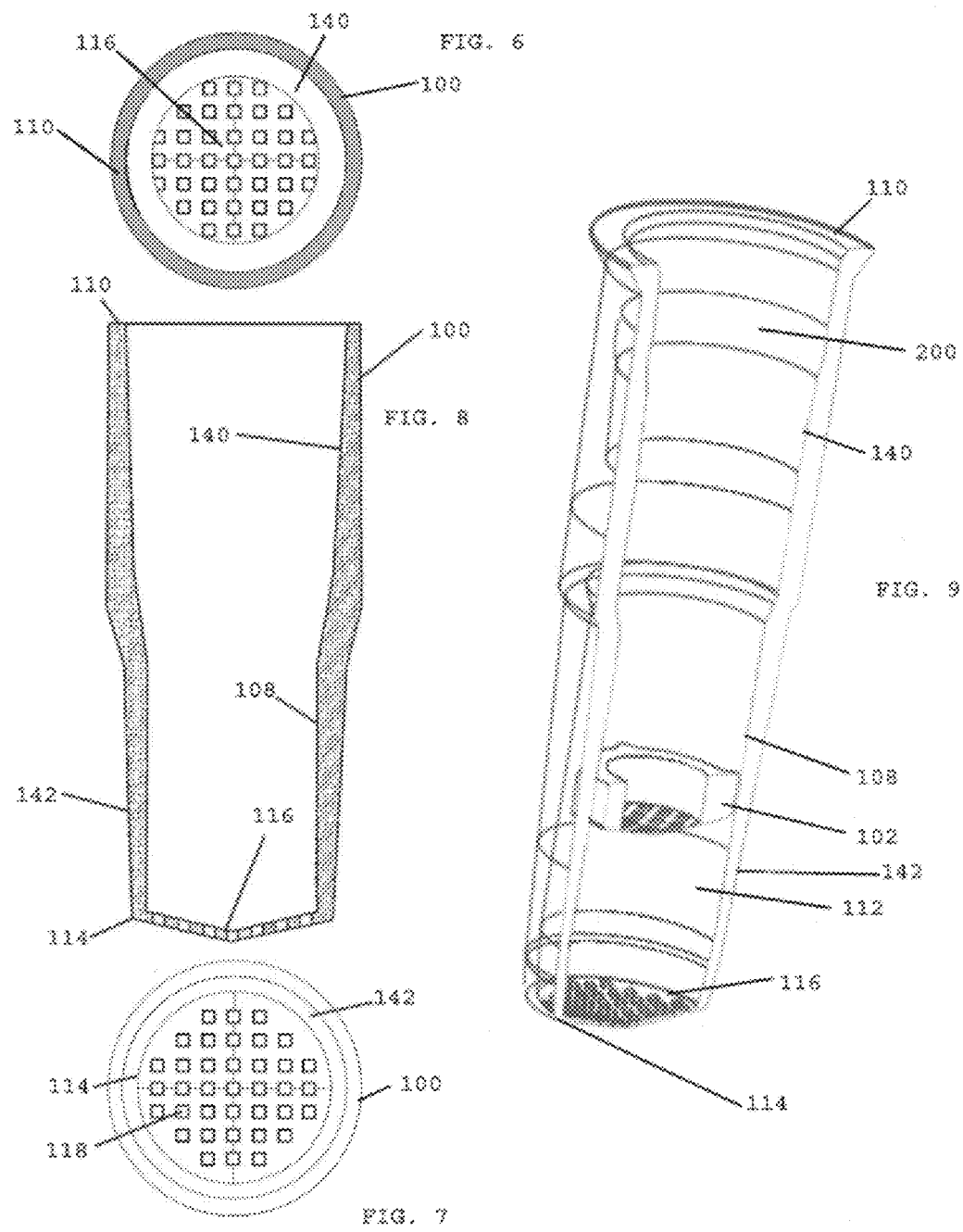

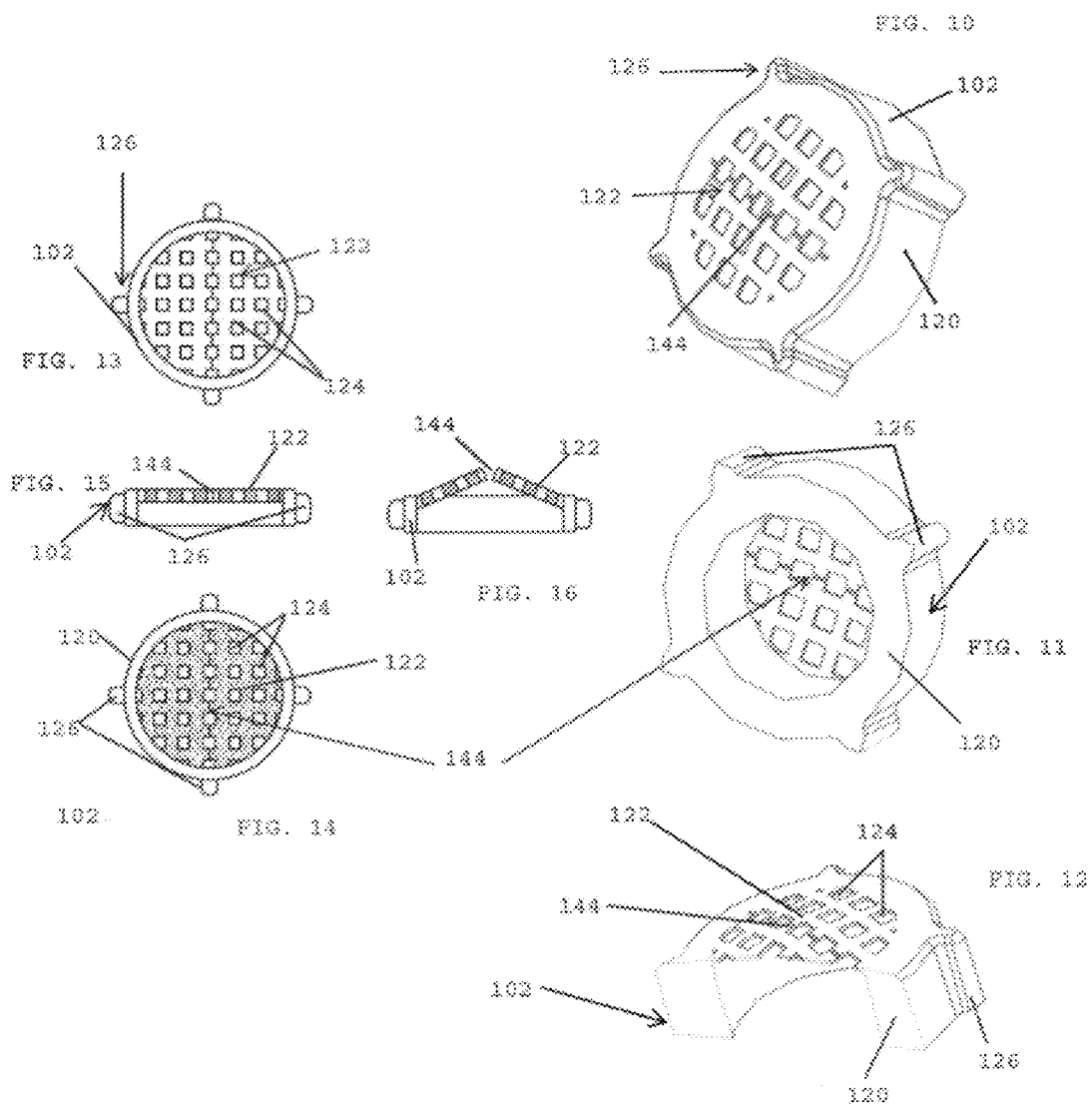

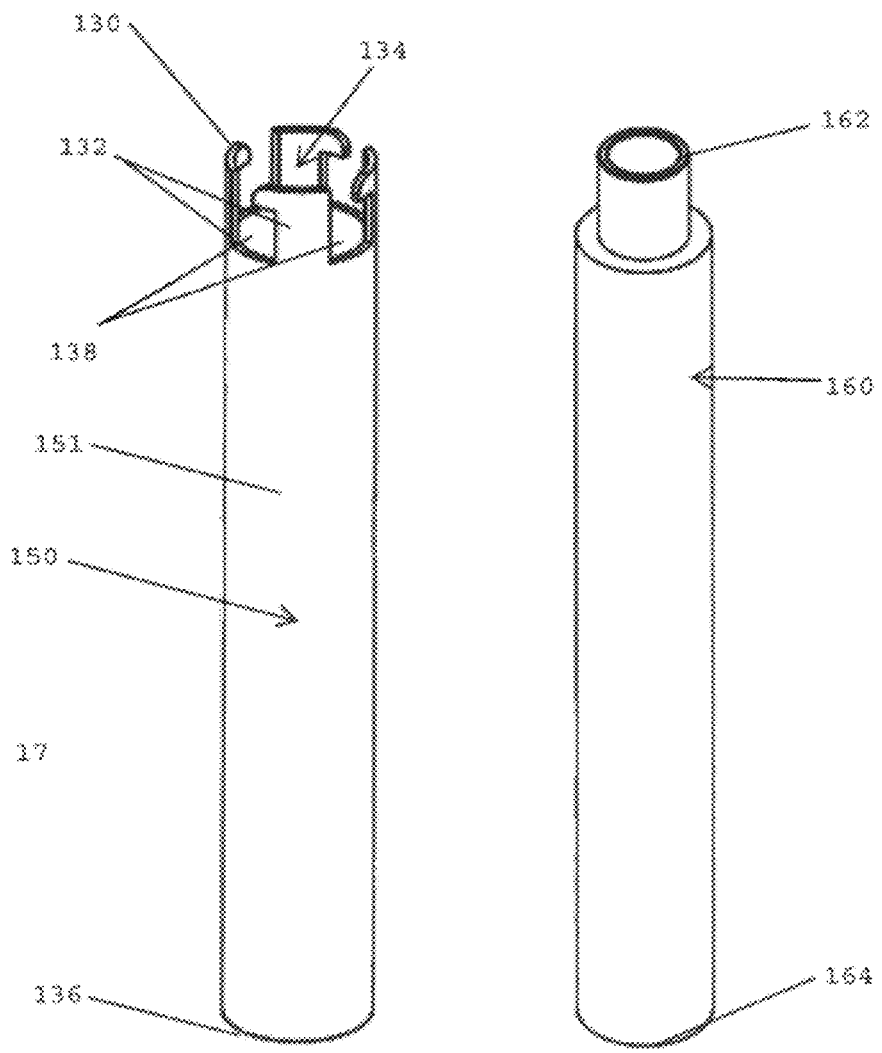

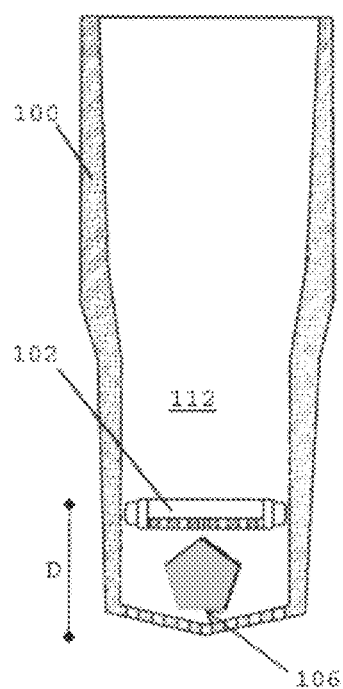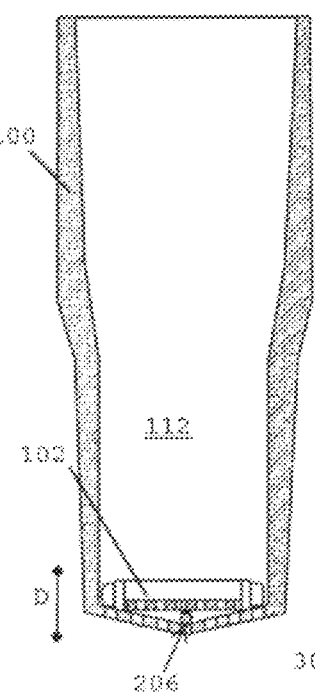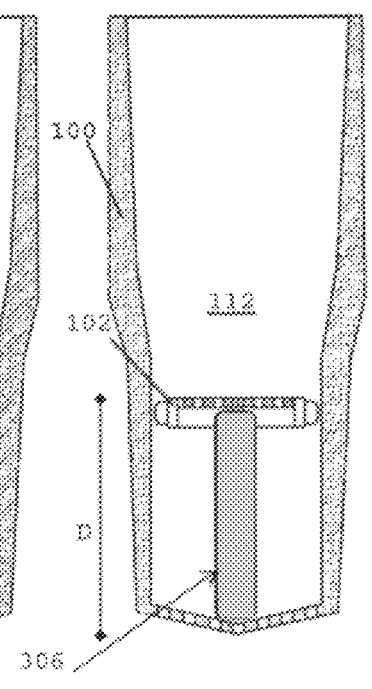

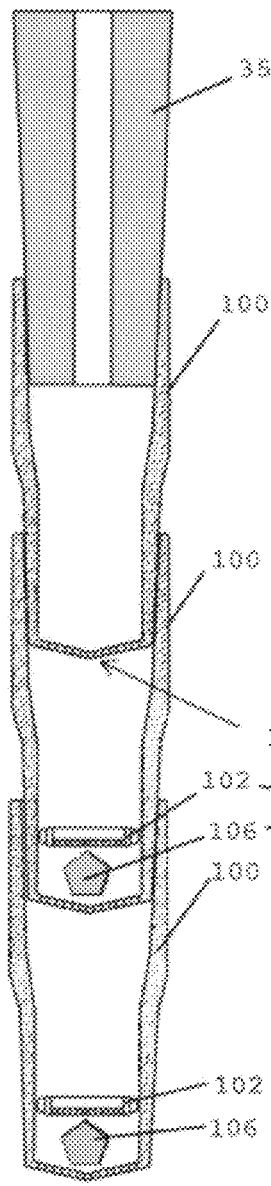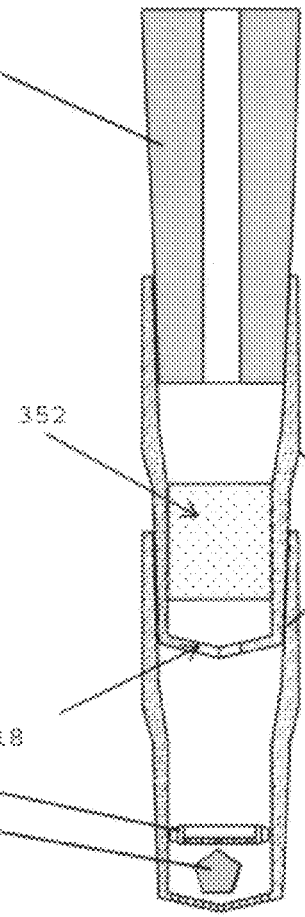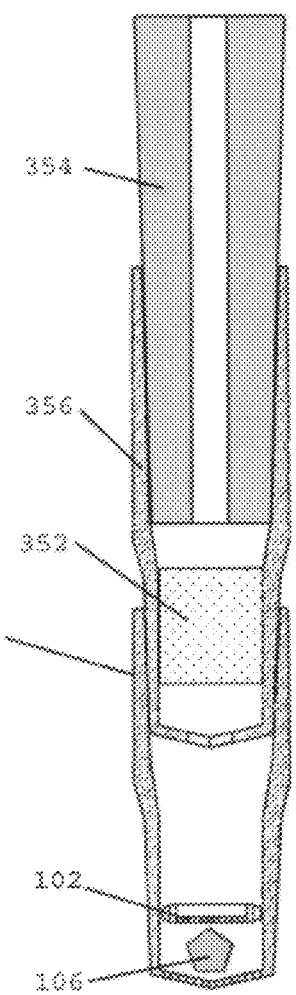

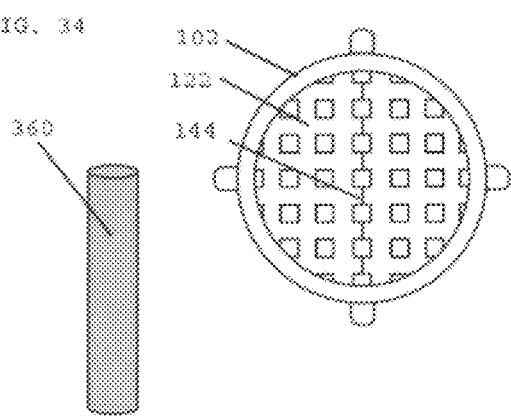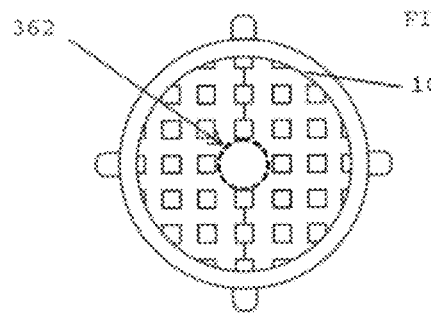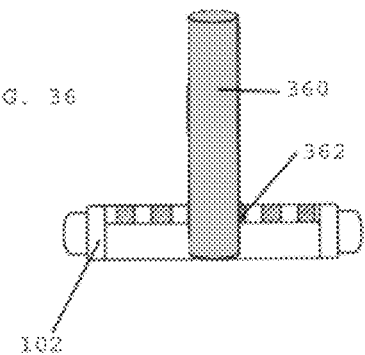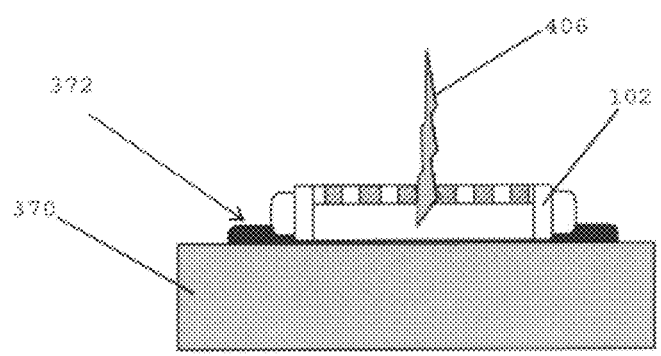

METHODS AND DEVICES FOR PREPARING MICROSCOPY SAMPLES

CROSS REFERENCE TO RELATED APPLICATIONS

This application seeks priority from U.S. Provisional Application Ser. No. 61/369,931 filed on Aug. 2, 2010, the disclosure of which is incorporated herein by reference in its entirety, for all purposes.

FIELD OF THE INVENTION

This invention is generally directed to apparatus and methods used to handle and prepare specimens for analysis with light and electron microscopes including especially transmission electron microscopes (TEM), scanning electron microscopes (SEM) and light microscopes (LM).

BACKGROUND OF THE INVENTION

Light Microscopes (LM), Transmission electron microscopy (TEM), Scanning Electron Microscopes (SEM) and other instruments are extensively used to understand the ultrastructure of a wide variety of synthetic and biological materials in numerous areas of science and technology. For example, light microscopy samples are used for research to identify the development of different organs in animals and plant. In addition, one major use of light microscopic samples is in the histophathologic examination of biopsy samples of tissues suspected of disease. TEM is used to study biological samples, metallurgical samples and many other types of materials. TEM images can be used to investigate the atomic structure of the objects, for example to identify areas of metal fatigue and to visualize the molecular and ultrastructure of cells, such images are capable of resolution down to 0.1 nm. SEM is similar to TEMs in that it uses electrons to create an image of the target/sample. However, the resolution of the SEM is on the molecular level (e.g., 100 nm-5 µm). Due to the SEM's ability to image bulk materials they can be used to image larger samples and samples that may or may not be sliced or sectioned.

Study objects for microscopy are prepared in multiple ways depending upon the type of material to be examined, and the type of microscopy to be used. Biological materials require special handling to preserve the structure of the material when it will be examined in the electron microscope, and secondarily to enhance or enable imaging.

Both SEM and TEM instruments perform their imaging in a vacuum (the absence or partial absence of air or other gases). Since biological materials are typically 50 to 95% water, if these were placed directly within the vacuum the water would evaporate and the specimen would collapse. Consequently both SEM and TEM samples have the water removed after the structure is strengthened with chemicals such as glutaraldehyde, formaldehyde, and osmium tetroxide.

TEM samples must be very thin (typically about 40 to 100 nm) in order for the electrons used for imaging to be "transmitted" or pass through the sample. To cut specimens into such thin sections the water is replaced with plastic resin that is hardened in place. This plastic supports the sample as it is sliced very thin using a device called an ultra-microtome.

Light microscope specimens, especially those of biological origin, are also often sectioned in order to provide cross-sections for viewing, and to allow photons (light) to be transmitted through the specimen. As with TEM, LM sections are also embedded to support the specimen during sectioning, however different generally softer plastics are used as the embedding material, as are paraffin wax and simply water that is frozen with additional materials to enable the ice to be softer, provide better support of the tissue, and reduce ice crystal damage during freezing.

While SEM specimens may be imaged in the bulk, that is without slicing into thin sections, with many specimens some slices or cross-sections are desired, such as to view interior structures. When these specimens are of biological origin, it is often necessary to perform many of the same chemical treatments as with TEM specimens in order to strengthen the structure for imaging in the SEM vacuum and to obtain cross-sections when these are desired.

The spatial orientation of cross-sections for many specimens can be very important in order to obtain the desired structural information, whether the specimens are to be examined with LM and TEM, and even SEM. For especially TEM and LM imaging of specimens to imaged as many thin slices, microscopists endeavor to orient the specimen in a plastic resin or other embedding media so that the cross-sectional slices are obtained in the desired orientation. These slices are then placed on microscope slides (for LM) or TEM grids (for TEM) to facilitate imaging through these thin cross-sections.

Many microscope specimens are imaged without the need for obtaining thin cross-sectional slices, but nonetheless where it is desired to obtain cross-sections in specific orientations. This is most common for SEM imaging, but sometimes desired for other types of microscopic analysis. For such imaging, as with SEM, the specimens are not commonly embedded in a plastic resin, but are nonetheless prepared by fluidic treatments with chemicals fixatives to preserve structure, solvents to dehydrate, and then commonly air-drying from solvents, or drying by the critical point. Freeze-drying is another method, where the specimens are also commonly first preserved with fixatives.

With TEM where specimens are sectioned, the standard process to obtain the proper orientation is to place or lay the fixed, dehydrated, and resin infiltrated specimens into a flat embedding mold filled with resin, and then place the mold into an oven for curing. These flat embedding molds are generally shallow wells prepared from silicone rubber, and provide no way to hold or retain the specimens in the proper orientation. Consequently, the specimen will often move during resin solidification. This often requires that specimens that are embedded in cured resin be sawed out and then glued onto other pieces of resin to provide the desired orientation. Of course, this is a time consuming extra step. Moreover, with fixed, dehydrated and resin infiltrated specimens it is often difficult to determine what the desired orientation is since the fixation process can make all regions of a tissue sample appear the same as typically viewed with the naked eye or even through a dissecting microscope which may be used in the preparation facility. For example, osmium tetroxide or potassium permanganate fixatives, as commonly used for TEM, generally makes all specimens the same uniform black color, unlike fresh tissue, partially fixed tissue, or tissue that has been stained. Thus, obtaining the proper orientation is often not possible, hence it is often not determined until one views specimen sections with the TEM.

With LM, where specimens are sectioned, the common process to obtain the proper orientation is place or lay the fixed, dehydrated, and/or paraffin infiltrated specimens into a flat embedding mold filled with melted paraffin. While it is easy to reorient specimens embedded in paraffin, by simply warming the paraffin until it melts, this is still a time-consuming step. Moreover, with fixed, dehydrated and paraffin infiltrated specimens it is often difficult to determine what the desired orientation is since the fixation process can make all regions of a tissue sample appear the same when viewed with the naked eye or with a dissecting microscope. Thus, obtaining the proper orientation is often not possible, hence it is often not determined until one views specimen sections with the LM.

With SEM where specimens require viewing in certain orientations, there is really no standard method to obtain the proper orientation other then to view the specimen with a dissecting microscope and mount it in the desired orientation. This is usually done with biological tissue after a specimen has been fixed, dehydrated, and dried by the critical point method, or fixed, dehydrated and air dried from a solvent, or fixed and freeze-dried, or otherwise treated to maintain structure in the vacuum of the SEM. With many specimens prepared by any of these fixation and preparation methods, all or most tissue regions appear the same when viewed with the naked eye or with a dissecting microscope which may be used in the preparation facility. Thus, obtaining the proper orientation is often not possible, hence it is often not determined until one views the specimen with the SEM.

Williamson et al, in U.S. Pat. No. 7,179,424, discloses a cassette for handling and holding tissue samples during processing for LM in, especially, histology laboratories. This tissue cassette has movable pegs that are used to create slots that can hold tissue in the desired orientation for sectioning. These can enable obtaining orientation prior to chemical processing. However, as with other, similar tissue cassettes, the cassette disclosed by Williamson includes a large volume of dead-space and provides little ability to visually inspect the samples. These cassettes are not suitable for specimens with dimensions on the order of 1 mm or smaller, as typically required for TEM and sometimes for LM. Furthermore, these cassettes are too large for preparing specimens for TEM, and are too thin and large for processing most specimens for TEM or SEM since these will not fit into apartatuti such as critical point dryers and freeze dryers.

Thus, the need exists for a low-cost device and method that allows for preparation of specimens in the proper orientation, and where such orientation can be visible throughout the process, where orientation can be preformed with fresh or stained tissue when tissue structure may be discerned to enable alignment, where the orientation of the specimen can be changed during the preparation process, and where the specimen is ultimately prepared in a configuration that is appropriate for TEM, LM and SEM with little or no additional steps.

Improvements to the conventional devices and methods of preparing specimens for microscopic analysis are desirable.

SUMMARY OF THE INVENTION

A device and method and system for preparing specimens for microscopic analysis is disclosed. The device provides a low-cost capsule that can be attached to a displacement pipette thereby filling the capsule with reagents desired for preparing the samples for microscopic analysis. Within this capsule is a mechanism that enables specimens to be readily and easily mounted in the proper orientation, and where such orientation can be visible throughout the process, and where the orientation of the specimen can be changed during the preparation process, and where the specimen is ultimately prepared in a configuration that is appropriate for TEM, LM and SEM with little or no additional steps.

BRIEF DESCRIPTION OF THE DRAWINGS

The accompanying drawing figures, which are incorporated in and constitute a part of the description, illustrate several aspects of the invention and together with the description, serve to explain the principles of the invention. A brief description of the figures is as follows:

FIGS. 1 to 4 are schematic diagrams of one embodiment of the invention showing the major components: a capsule that holds the specimen (shown in cross section) called a Specimen Holder Micro-pipette (SHMP), the SHMP Insert that is placed within the SHMP capsule to retain the specimen (shown in top view and cross-sectional side view) and the SHMP Insertion Tool that is used to position the insert within the capsule FIG. 1 is a side cross-sectional view of a capsule according to the present disclosure.

FIG. 2 is a top view of an insert according to the present disclosure for use with the capsule of FIG. 1.

FIG. 3 is a side view of the insert of FIG. 2.

FIG. 4 is a side view of a tool according to the present disclosure for inserting the mesh insert of FIG. 2 within the capsule of FIG. 1

FIGS. 6 to 9 are schematic diagrams of one embodiment of the invention showing a cross-section of the SHMP and showing both a top view of the SHMP and a bottom view.

FIG. 6 is a top view of the capsule of FIG. 1.

FIG. 7 is a bottom view of the capsule of FIG. 1.

FIG. 8 is a side cross-sectional view of the capsule of FIG. 1.

FIG. 9 is a side perspective view of the capsule of FIG. 8 with the insert of FIG. 2 positioned within.

FIGS. 10 to 16 are schematic diagrams of one embodiment of the present disclosure showing the insert of FIG. 2 in more detail.

FIG. 10 is a first perspective view of the insert of FIG. 2.

FIG. 11 is a second perspective view of the insert of FIG. 2

FIG. 12 is a perspective cross-sectional view of the insert of FIG. 2.

FIG. 13 is a top view of the insert of FIG. 2.

FIG. 14 is a bottom view of the insert of FIG. 2.

FIG. 15 is a side cross-sectional view of the insert of FIG. 2.

FIG. 16 is a side cross-sectional view of the insert of FIG. 2, showing that the integral slit in a central portion of the insert may be flexed open.

FIGS. 17 and 18 are schematic diagrams of elements of a second embodiment of an insertion tool for placing an insert and flexing the insert that is place into the capsule according to the present disclosure.

FIG. 17 is a side perspective view of an outer portion of the second embodiment insertion tool according to the present disclosure.

FIG. 18 is a side perspective view of an inner spreader portion of the second embodiment insertion tool according to the present disclosure, with the inner portion configured to fit within the outer portion.

FIG. 19 is a side perspective view of the tool of FIGS. 17 and 18 holding the insert of FIG. 2 in preparation for positioning the insert within the capsule of FIG. 1.

FIG. 20 is a closer perspective view of the insert held by the tool as shown in FIG. 19.

FIG. 21 is a perspective cross-sectional view of the insert held by the tool as shown in FIG. 19.

FIGS. 22 to 24 are schematic diagrams of one embodiment of the capsule and insert of the present disclosure showing that the insert can be placed in different positions and orientation to accommodate various specimens. Each diagram shows an indicator along one side showing the fluid level within the capsule required to immerse the specimen to prepare the specimen for analysis.

FIG. 22 is a side cross-sectional view of the capsule and insert with a first specimen positioned within the capsule.

FIG. 23 is a side cross-sectional view of the capsule and insert with a second specimen positioned within the capsule.

FIG. 24 is a side cross-sectional view of the capsule and insert with a third specimen positioned within the capsule.

FIG. 25 is a diagrammatic view of a sequence of steps according the present disclosure for placing a first specimen for analysis within the capsule of FIG. 1, and using the tool of FIGS. 17 and 18 to position the insert of FIG. 2 within the capsule and secure the specimen within the capsule.

FIG. 28 is a diagrammatic view of a sequence of steps according to the present disclosure that shows an apparatus for assisting the use of the spreading function of the tool of FIGS. 17 and 18 to position a specimen within the slit of the insert.

FIGS. 31 to 33 are schematic representations of embodiments of the present disclosure that illustrate that several capsules may be stacked together and engaged by one pipetter.

FIG. 31 is a side cross-sectional view of a pipetter with an empty capsule directly adjacent the pipetter tip and additional capsules including specimens mounted to the empty capsule.

FIG. 32 is a side cross-sectional view of the pipetter with a capsule including a filter adjacent the pipetter and an additional capsule including a specimen mounted to the filter capsule.

FIG. 33 is a side cross-sectional view of a second pipetter corresponding to a different standard with an adapter capsule including a filter adjacent the second pipetter and an additional capsule including a specimen mounted to the adapter filter capsule.

FIGS. 34 to 36 illustrate adaptation of the insert of FIG. 2 according to the present disclosure for use with a rod shaped specimen.

FIG. 34 is a top view of the insert of FIG. 2 with a rod shaped specimen in perspective view positioned adjacent the insert.

FIG. 35 is a top view of the insert of FIG. 2 with a cut out for receiving the rod shaped specimen form in the slit.

FIG. 36 is a side view of the insert of FIG. 35 with the rod shaped specimen positioned within the cutout and slit and prepared for placement within a capsule according to the present disclosure.

FIG. 37 is a side cross-sectional view of the insert of FIG. 2 with a specimen positioned within the slot, and the insert mounted to a base for imaging and/or analysis outside of a capsule.

DETAILED DESCRIPTION OF THE EXEMPLARY EMBODIMENTS

Figure 5:
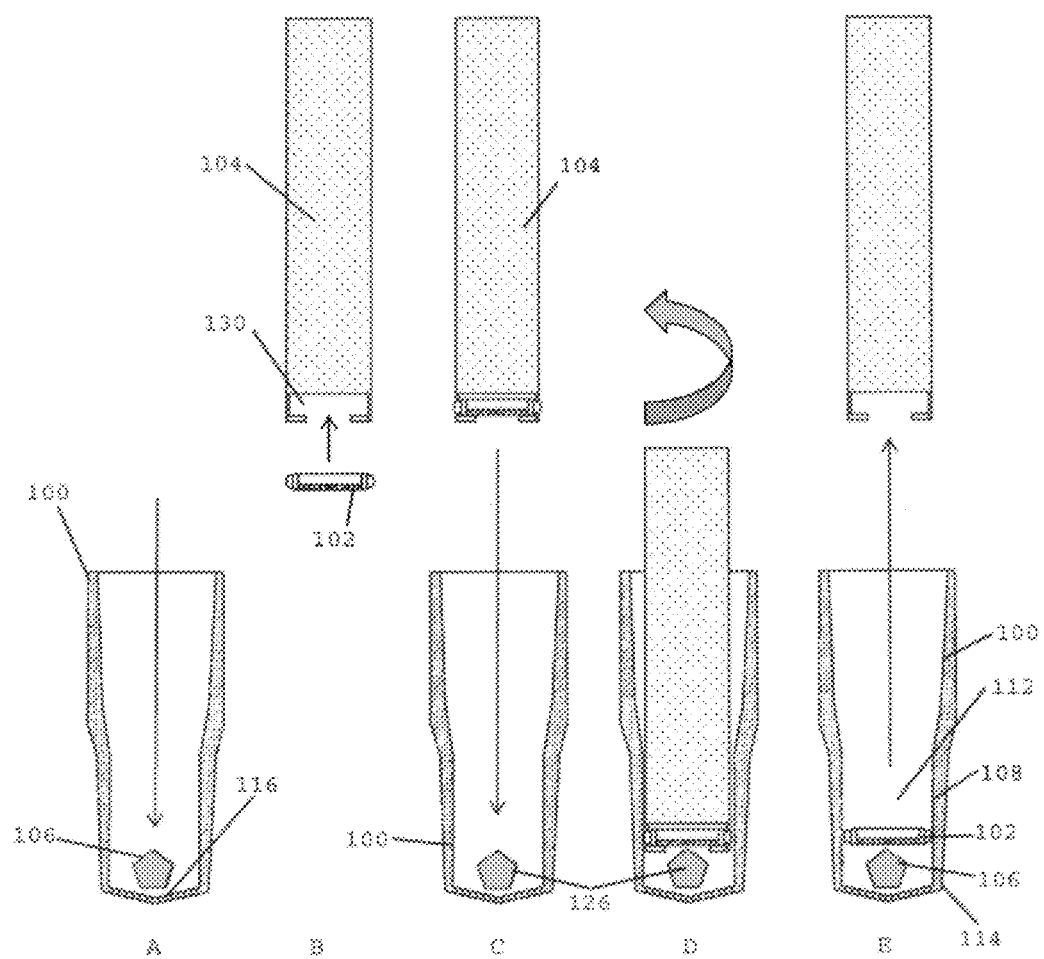
FIG. 5 is a diagrammatic view of a sequence of steps according the present disclosure for placing a specimen for analysis within the capsule of FIG. 1, and using the tool of FIG. 4 to position the insert of FIG. 2 within the capsule and secure the specimen within the capsule.

The present disclosure describes devices and systems to improve processing and handling of TEM specimens, LM specimens, SEM specimens, and certain other types for specimens. It also has applications beyond microscopy including tissue culture.

Before the present invention is described, it is understood that this disclosure is not limited to the particular methodology, protocols, and reagents described herein, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference for the purpose of describing and disclosing the chemicals, cell lines, sample preparation methods, animals, instruments, statistical analysis and methodologies which are reported in the publications which might be used in connection with the disclosure. Nothing herein is to be construed as an admission that the disclosure is not entitled to antedate such disclosure by virtue of prior invention.

In General

The present disclosure provides devices and methods and systems for preparing samples or specimens for microscopic analysis. The device may include a reservoir that can be attached to a displacement pipette thereby filling the reservoir with reagents desired for preparing the samples for microscopic analysis, such as by transmission electron microscopy. In other embodiments, the sample may be a light microscope specimen. In still other embodiments the sample may be a specimen for analysis by scanning electron microscopy. And, in still other embodiments the device may hold specimens for non-microscopy related applications such as tissue or organ culture.

FIGS. 1 to 4 are schematic diagram of one embodiment of the invention showing the three major components of the system: a capsule 100 that may be used to contain or hold a specimen for processing, herein referred to as a Specimen Holder Micro-pipette (SHMP) capsule, a SHMP insert 102 that may be placed within SHMP capsule 100 to retain the specimen and a SHMP insertion tool 104 that may be used to position insert 102 within capsule 100. Capsule 100 may include a first open end 110 allowing access into a reservoir 112 defined within the capsule. A second opposite end 114 may include one or more apertures 118 and may be shaped to encourage a specimen within the reservoir to rest in the center of a bottom 116 defined for the reservoir within the capsule. Reservoir 112 may also include an inner wall 108.

Insert 102 may include a generally circumferential base 120 and a web 122 extending across an open center of the base with one or more apertures 124 extending therethrough. A plurality of tabs 126 may extend outward from the base to position the insert within the reservoir of the capsule and engage inner walls of the reservoir Insertion tool 104 may include an insert engaging end 130 with a plurality of arms 132 for releasably engaging insert 102 within an opening 134. Preferably tabs 126 would extend beyond an outer wall 136 of each arm 132 so that the tabs would engage inner wall 108 of the reservoir and hold the insert within the reservoir permitting the insertion tool to be withdrawn, leaving the insert secured within the reservoir.

FIG. 5 illustrates one possible basic mode of operation of the device of the present disclosure. A specimen 106 may be placed into SHMP capsule 100. SHMP insert 102 may be loaded onto insert engaging end 130 of insertion tool 104. Insertion tool 104 with loaded insert 102 may be slid into reservoir 112 of SHMP capsule 100. Tabs of insert 102 may engage inner wall 108 of reservoir 112 to secure the insert within the reservoir. Insert 102 may be released from insertion tool 104 by rotation, and tool 104 may then be removed from the reservoir, leaving insert 102 in position within capsule 100 to hold specimen 106 in place adjacent bottom 116 and second end 114.

FIGS. 6 to 8 illustrate one embodiment of the capsule 100 in cross-section of the SHMP capsule as well as a top view of the SHMP capsule and a bottom view. There may be one or more holes or apertures 118 at the second end 114 of the capsule 100 with a size that may be preferably smaller than the specimens to be held, but not so small as to inhibit the free flow of fluids into and out of the SHMP capsule. For most common electron microscope specimens the holes or apertures 118 may be preferably between 200-300 um across. For use with specimens such as cells, the holes 118 may be as small as about 5-10 um. The shape of the second end 114 and the bottom 116 of the SHMP capsule may be wedged, tapered or curved to facilitate the centering of specimens of different shape at the apex of the bottom. An upper portion 140 of the reservoir adjacent first end 110 may be tapered or otherwise shaped on the inside to receive a displacement pipetter. The inside lower portion of the walls 108 within the reservoir may preferably have sides that are nearly parallel so that the insert can be placed at any location within the capsule above or spaced apart from bottom 116. An outside 142 of a lower portion of the SHMP capsule adjacent second end 114 may be tapered to enable coupling into the inside of the upper portion 140, or with a standard pipette tip. Shown in FIG. 9 is a transparent cross-sectional drawing of a second embodiment 200 of a capsule according to the present disclosure with an insert 102 positioned within reservoir 112.

FIGS. 10 to 16 illustrate a schematic diagram of one embodiment of the disclosure showing SHMP Insert 102 in more detail. The top view shows the tabs 126 that press against inside walls 108 of the reservoir of SHMP capsule 100 and provide a friction fit of the insert within the reservoir. The tabs may also assist in the engagement of insert 102 with insertion tool 104 to enable the insert to be placed and positioned within the capsule. The insert may have holes or apertures 124 to enable fluid flow in the web 122, and these holes may be sized similarly to those in the SHMP bottom, on the order of 200-300 um for most specimens. Tabs 126 may extend from base 120 of insert 102 also for about 200-300 um to enable fluid flow around the insert within the reservoir of capsule 100 while maintaining openings of a small enough size to also retain most specimens. The number of flanges may be preferably small, such as but not limited to numbering 4 as shown in this embodiment, so that when the SHMP capsule is filled with resin and the resin filled capsule is clamped in a microtome chuck for sectioning, considerable resin extends around the insert so that the insert does not provide a weak point in the resin used to hold the specimen.

Insert 102 preferably may include a slit 144 so that the web 122 can be flexed open (as shown in FIG. 16). Web 122 is preferably made of a resilient deformable material so that the slit may be flexed open to permit the insertion of the specimen into the slit. The insert can then be allowed to return to its relaxed state to then clamp onto the specimen and secure the specimen to the insert. Web 122 is also thin so that it can be cut by users to provide a clamp or opening suitable for clamping specimens of various sizes, as will be discussed below with regard to FIG. 35.

FIGS. 17 and 18 illustrate two elements, outer or insertion portion 150 and inner or spreader portion 160 that may comprise a different embodiment of the insertion tool 104. Outer portion 150 may be a generally hollow tube 151 with insert engaging end 130 with flanges or arms 132 shaped to hold insert 102 by engaging and holding tabs 126 within openings 138 defined between arms 132. An outside diameter of the outer portion 150 preferably approaches an inside diameter defined by walls 108 within of reservoir 112 of SHMP capsule 100, so that when the outer portion is inserted into the SHMP, the outer portion becomes centered and aligned within the reservoir of the SHMP capsule. An inside diameter of outer portion 150 is preferably slightly greater than the diameter of the base of the insert minus tabs 126 extending outward. A second open end 136 opposite insert engaging end 130 may provide a path for insertion of inner portion 160 within hollow tube 151. It should be noted that outer portion 150 may be used alone as an insertion tool when only the positioning of insert 102 within capsule 100 is desired and no deflection of the insert to open slit 144 is needed.

Inner or spreader portion 160 preferably has an outside diameter that is slightly less than the inside diameter of the outer portion 150 so that the inner portion can freely slide within the outer portion while remaining centered. A tip 162 of the inner portion is preferably shaped so that it can extend into engagement with an insert held by outer portion 150. When pressed against the insert, tip 162 of inner portion 160 can cause web 122 of insert 102 to deflect and separate at slit 144, causing the slit to open to permit the insertion of a specimen.

Figure 19:
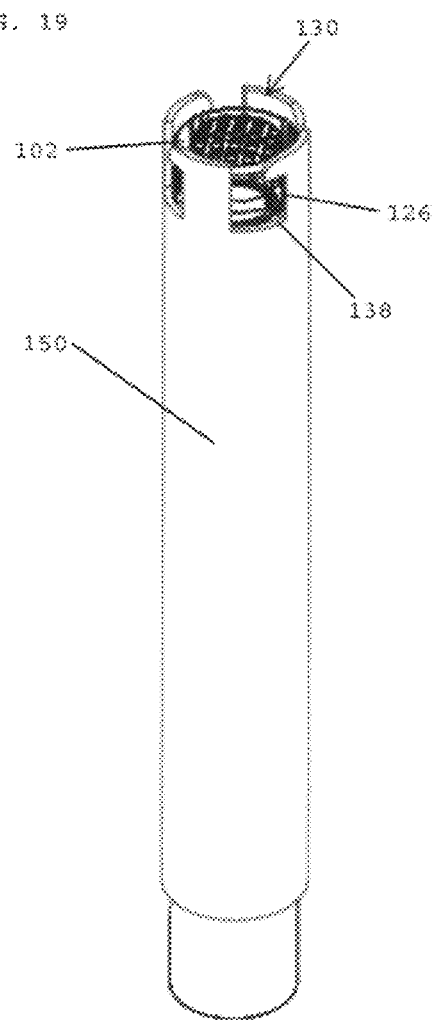
FIGS. 19 to 21 are schematic diagrams of one embodiment of the present disclosure showing several views of an insert of FIG. 2 held by the tool of FIGS. 17 and 18.
Figure 20:
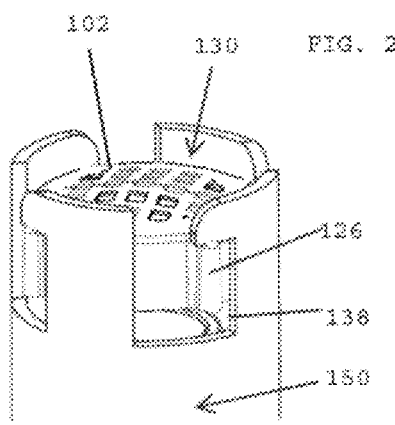
Figure 21:
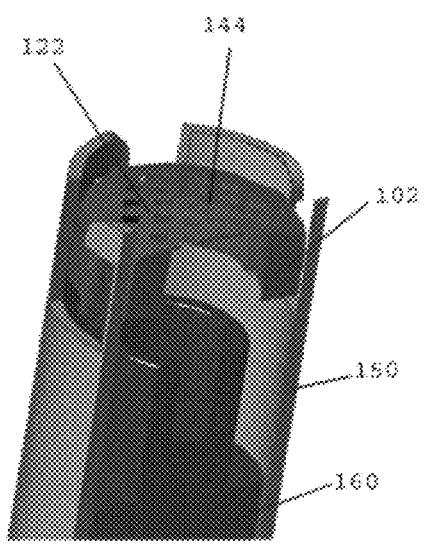

FIG. 19 illustrates an insert 102 held within insert engaging end 130 of outer portion 150. Tabs 126 are shown extending through openings 138 to hold the insert to the outer portion. FIG. 20 is a closer view of the insert within insert engaging end 130. In FIG. 21, spreading or inner portion 160 is shown positioned within outer portion 150 and in position to be advanced so that tip 162 engages web 122 of insert 102 to open slit 144.

FIGS. 22 to 24 illustrate that SHMP insert 102 can be placed in different positions within reservoir 112 of capsule 100 to accommodate specimens 106, 206 and 306 of different sizes and shapes. The Insert can also be placed "up side down" to accommodate long specimens, as shown in FIG. 24. For each of the different size specimens, there is a indicator adjacent the capsule showing the depth of fluid D required to fill the capsule sufficiently to process the specimen with the reservoir. By using the insert to hold the specimen toward the bottom of the capsule, the amount of liquid needed to process a specimen can be kept to a minimum based on the specimen size.

FIG. 25 illustrates a process that may be used to position a specimen 106 within the reservoir of a capsule according to the present disclosure so that the specimen is properly orientated. The schematic shows the various steps in cross section. Note that the devices and methods of the present disclosure permit a wide variety of shapes and sizes of specimens to be positioned within a capsule and oriented as desired for processing and analysis. The method or process of FIG. 25 is illustrative only and is intended to show one possible method of positioning and orienting a specimen according to the present disclosure. Step 1 is the placing and engaging of an SHMP insert 102 into the insertion tool 104. (The inner portion or spreading portion is shown in this sequence but its spreading function is not utilized.) Web 122 is now held in a horizontal position providing easy access to placing a suitable specimen in the proper orientation. (The figure shows web 122 (serving as an insertion face) placed "up," however it is also possible to place it "down" to accommodate long specimens or specimens that are otherwise more conveniently retained in this orientation of the insert, as shown in FIG. 24, above. Some specimens may just be balanced on the web (as shown in steps 2 and 3), while others may be temporarily or permanently glued to the web using, for example; a droplet of water, buffer solution, or glycerol solution to hold the specimen using surface tension; a low melting temperature agar solution; a glue such as cyanoacrylate which will hold the specimen and then be dissolved during subsequent and appropriate chemical treatment of the specimen, or by other glues appropriate for the specimen and the processing chemistry and physics. Once the specimen is placed on the web, the SHMP capsule may then be slid over the insert (step 4) until it gently entraps the specimen between the inside of the SHMP bottom 116 (SHMP is upside down) and the insert. The SHMP capsule with the specimen and insert inside may then be removed by rotating the SHMP (steps 5-6) to disengage the insert from the insertion tool. The SHMP capsule with the specimen and insert inside may then be processed for microscopy.

Figure 26:
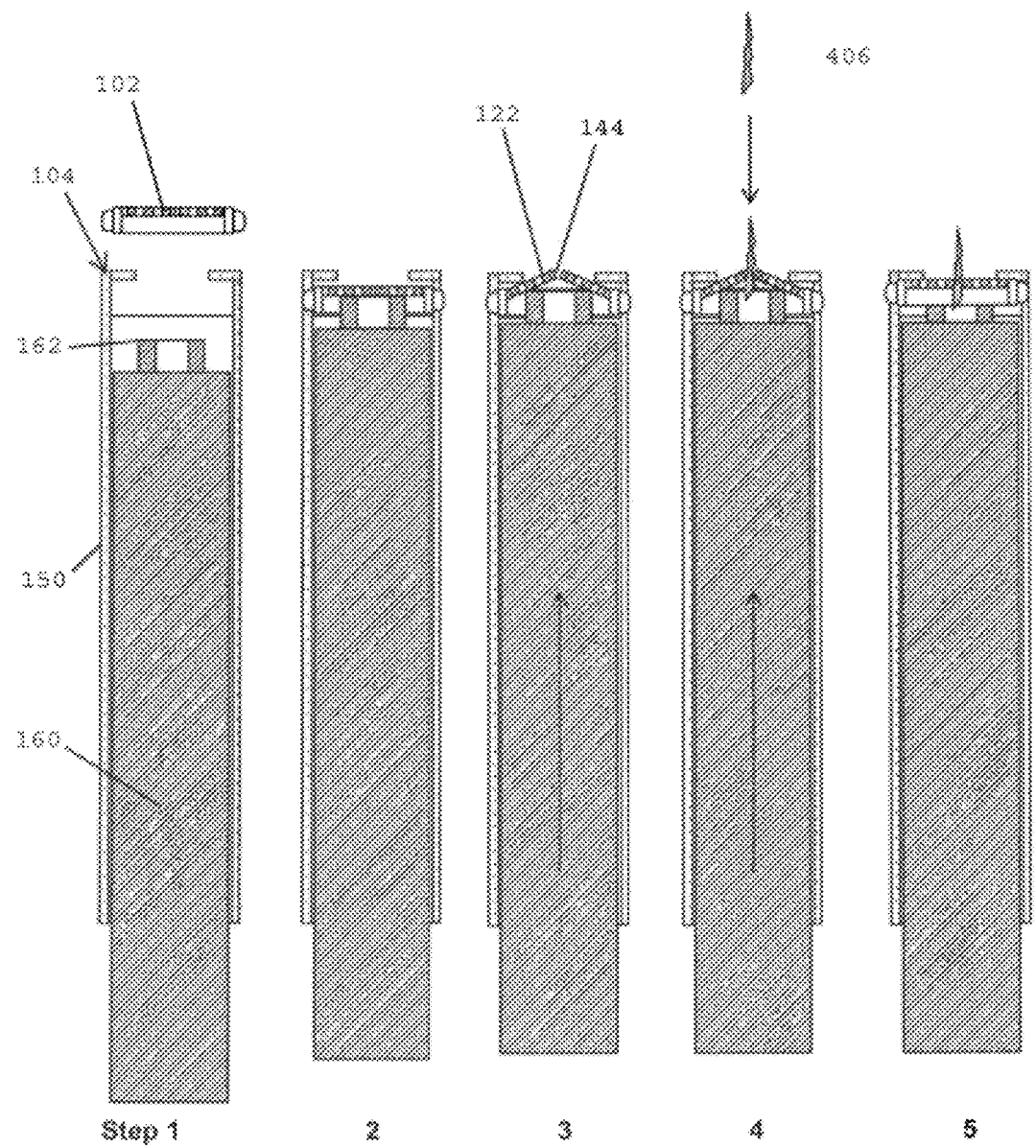
FIG. 26 is a diagrammatic view of a sequence of steps according the present disclosure for placing a differently shaped specimen for analysis within the capsule of FIG. 1, and using the tool of FIGS. 17 and 18 to position the insert of FIG. 2 within the capsule and secure the specimen within the capsule, with the spreading tool used to open the slit within the insert to accept and hold the specimen.
Figure 27:
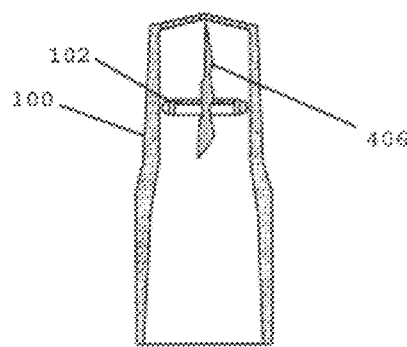
FIG. 27 illustrates the differently shaped specimen held by the insert as shown in FIG. 25, with the insert and specimen positioned within the capsule of FIG. 1.

FIG. 26 illustrates the use of insertion tool 104 so as to open slit 144 of insert 102 to permit the insertion and pinching or capture of the specimen by the insert, showing one of many possible methods for placing specimens within an SHMP capsule so that the specimen is properly orientated. FIG. 26 shows the various steps in cross section. In this mode of operation, a suitable specimen 406 may be one where it is convenient to pinch the specimen. Step 1 is the placing and engaging of an SHMP insert 102 into insertion tool 104. In step 2 the web 122 is now held in a horizontal position providing easy access to permit inserting a suitable specimen in the proper orientation. In step 3, the inner portion or spreading portion 160 of insertion tool 104 may then be moved "up" relative to the outer portion 150. (Alternatively, the outer portion may be moved "down" relative to the inner portion.) This action causes pressure to be exerted on the back side of web 144 of insert 102 by the tip 162 of inner portion 160, which in turn causes slit 144 on the web to separate. The specimen may then be inserted into the slit to the desired depth (step 4). The position of the outer portion relative to the inner portion may then be reversed to that in Step 2. At this point (Step 5), the specimen is now held by the insert. As shown in FIG. 25, a SHMP capsule may then be slid over the insert and the SHMP capsule with the specimen and insert inside may then be removed by rotating the SHMP capsule relative to the insertion tool to disengage the insert from the insertion tool FIG. 27 illustrates a desired orientation and positioning of a long specimen 406 into an insert 102 and the positioning of the insert within a capsule 100. This illustrates a means to handle long specimens and place the analysis portion in close proximity to the end of the capsule. The figure shows that a substantial portion of the specimen that is not generally intended to be analyzed, is not between the end of the capsule and the insert 102.

FIG. 28 illustrates a series of steps to capture specimen 406 within insert 102 and to position the insert within capsule 100 and shows an apparatus 186 for enabling the spreading function. The inner or spreading portion 160 may be attached to a base 180 that supports the inner portion generally vertically. The outer portion may then be slid over the inner portion. An insert may be engaged by the outer portion. Specimens may be placed on the insert as shown in FIG. 25 for loading into SHMP capsules as also shown in FIG. 25. To utilize the specimen pinching function, as shown in FIG. 26, the outer portion of the insertion tool 150 may then be pushed down by holding the outer portion with fingers 182 or a suitable tool. Once the specimen 406 is properly positioned into or on top of the insert, the insertion tool is no longer pushed down, thus engaging the pinching function of the insert. An SHMP capsule may then be slid over the insert to the proper depth for the specimen, rotated to disengage the insert, and then removed for processing.

Figure 29:
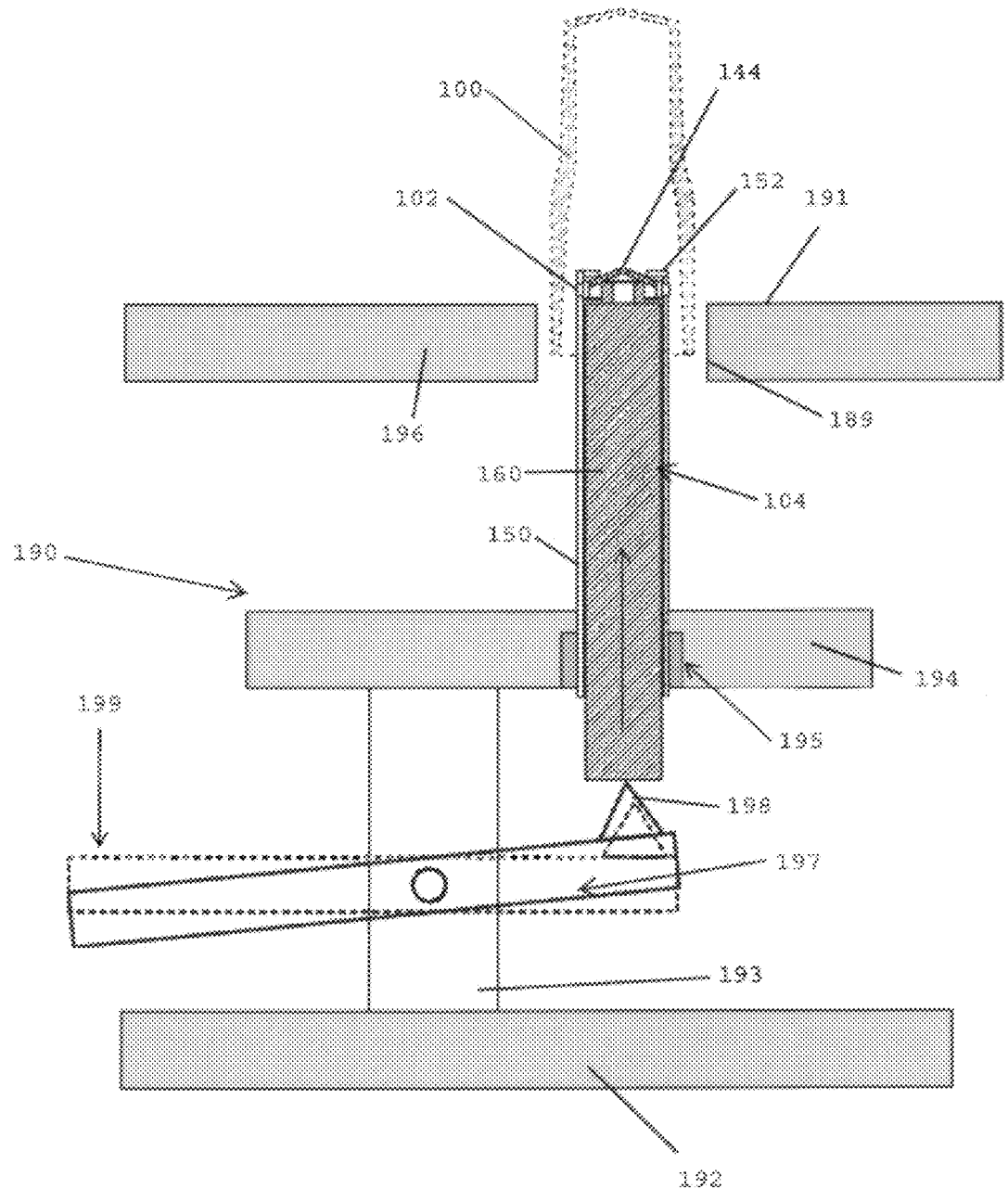
FIG. 29 is a schematic diagram of one embodiment of the invention showing an apparatus for enabling the spreading function that uses a lever.

FIG. 29 illustrates a schematic diagram of an apparatus or system 190 for enabling the spreading function of insertion tool 104 that uses a lever 197 to apply upward force on insertion tool spreader 160. In this embodiment the insertion tool outer part 150 may be held stationary using a clamp 195. A base 192 provides a sturdy lower element for apparatus 190 with an upward member 193 supporting a second platform 194 spaced vertically above base 192. The inner or spreading portion 160 then slides up and down within the outer portion 150 of insertion tool 104 due to the action of lever arm 197. A first end 198 of the lever 197 is configured to engage the inner portion of insertion tool 104 while a second opposed end 199 of lever 197 provides a site for downward pressure to be applied to urge the inner portion upward. The dotted lines show the lever in the location where the spreading inner portion is not engaged, while the solid lines show the lever engaging the spreading function.

An upper specimen processing surface 191 of an upper platform 196 may be configured to provide ease of processing and engagement of specimens. Preferably, insert engagement end 152 of insertion tool 104 would extend through an opening 189 in platform 196 so that an insert 102 held by the insertion tool would be closely positioned to surface 191. Opening 189 is also preferably sized so that once a specimen is held within slit 144 of insert 102, a capsule 100 may be placed over the insert and the insertion tool to position the insert and specimen within the capsule. Rotation of the capsule would then release the insert from engagement with insertion tool 104, permitting removal of the capsule, insert and specimen from apparatus 190.

Figure 30:
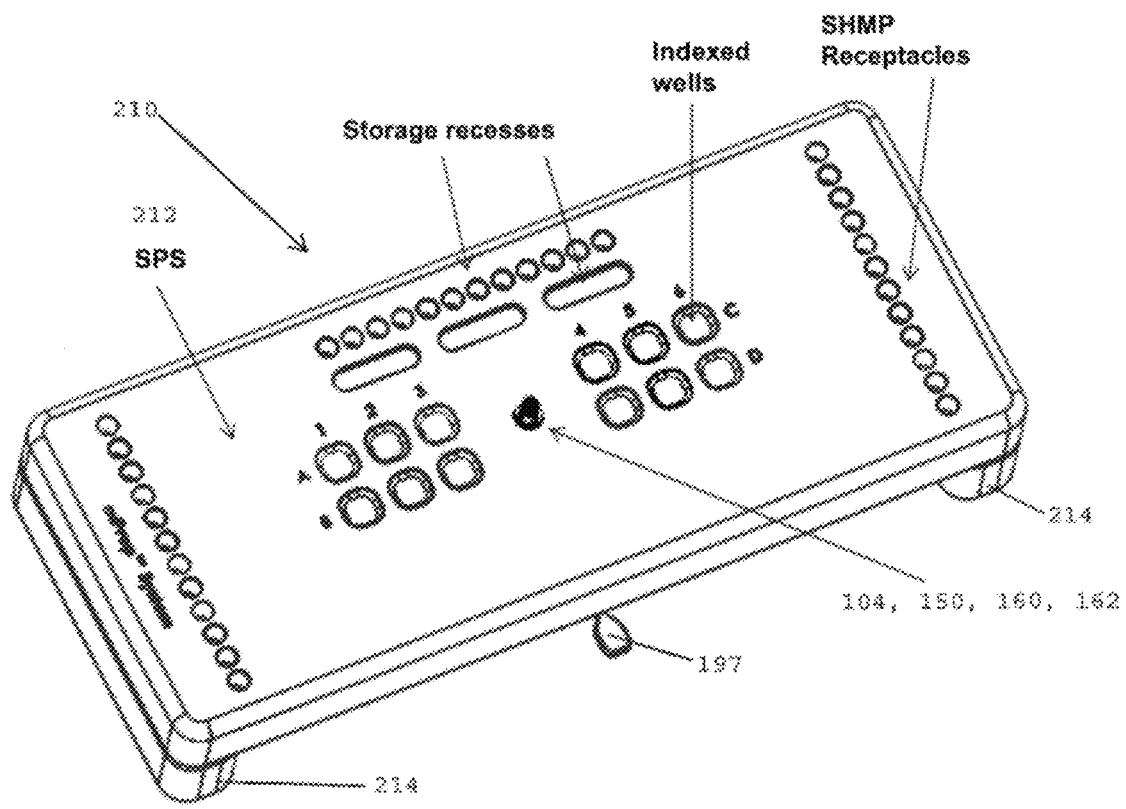
FIG. 30 is a perspective view of one embodiment of the invention that incorporates the lever action spreading function shown in FIG. 29.
Figure 38:
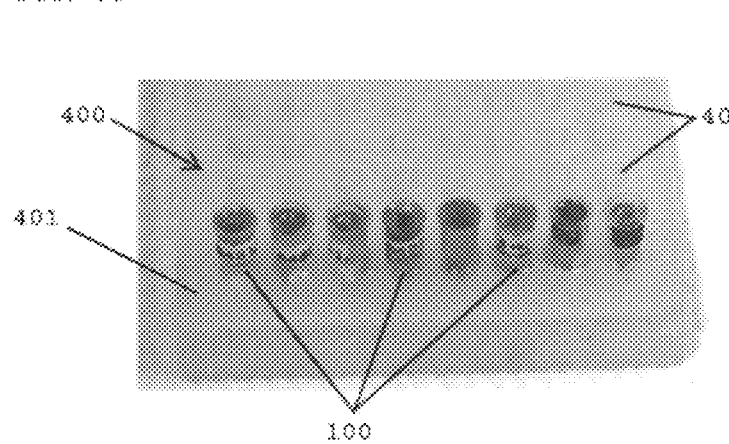

FIG. 30 illustrates a first embodiment 210 according to the present disclosure that may incorporate the lever action spreading function shown in FIG. 29. This apparatus 210 may provide a convenient workstation for microscopists to process and mount specimens into SHMP capsules for processing. The lever action spreading mechanism as shown is hidden underneath the specimen processing surface SPS 212, except for the portion of the insertion tool 104 that engages inserts 102, and the tip of the inner portion that also engages the insert. Lever 197 that engages the spreading inner portion may be at the front of apparatus 210 for convenient operation. The insertion tool mechanism may be centered in the workstation apparatus 210 so that it is easily and conveniently viewed using a suitable stereo or dissecting microscope. The insertion tool is only slightly above the plane of the specimen-processing surface so that specimen preparation (such as cutting) occurs in nearly the same optical plane as placing the specimen onto or into the Insert that is engaged in the insertion tool. Adjustable legs 214 on both sides of the workstation enable it to straddle the base of most stereomicroscopes. As desired, the widely spaced legs enable the workstation to be slid over the stereomicroscope base to enabling viewing different portions of the specimen processing surface SPS. The specimen processing surface SPS is preferably flat and made from polypropylene, polyethylene, or other materials to provide a suitable surface for cutting specimens, to not absorb water or buffers, and for ease of cleaning. Wells in the surface may be used to retain specimens in buffer or water or other fluids, are shallow with sloping sides to enable cutting and manipulating specimens held within and allow easy clean out, and may be indexed as shown. Storage recesses may be used to hold Inserts and SHMP capsules prior to use. Receptacles for SHMP capsules are present at both ends of the workstation to provide a location for placing SHMP capsules loaded with specimens while additional SHMP capsules are loaded. The receptacles can be filled with water or buffer or other fluids to keep samples in good condition. The spacing between the 12 receptacles may place the SHMP capsules at the proper spacing for mating with multi-channel pipetters that hold 8 or 12 or other numbers of pipette tips of the proper size.

FIGS. 31 to 33 illustrate an embodiment of the present disclosure which shows a cross sections that illustrate that several SHMP capsules may be stacked together and then onto a pipetter to enable the simultaneous processing of specimens in two or more SHMP capsules. FIG. 31 shows a plurality of capsules 100 attached to a pipetter 350. Pipetter 350 is positioned within the first end of the uppermost capsule 100. The second end of the uppermost capsule 100 is received within the first end of the next capsule 100, with the second end of the middle capsule 100 engaged within the first end of the lowest capsule 100. As shown, the uppermost capsule may or may not contain a specimen for processing. The remaining lower capsules are shown with specimens 106 positioned beneath inserts 102 for processing.

FIG. 32 shows the uppermost position engaging the pipetter, an SHMP capsule 100 that is modified to retain a filter to provide protection for the aspiration of reagents into the pipetter mechanism. Shown is a second embodiment of an SHMP used to provide a filter, where the holes in the SHMP capsule are much larger that that required to retain small specimens, since specimen retention is not necessary.

FIG. 33 shows an adapter capsule 356 according to the present disclosure which is configured to engage a pipetter 354 that conforms to a different size or shape standard as compared to pipetter 350. Adapter capsule 356 permits capsules 100 to be used with pipetters conforming to different size or configuration standards so that standardized specimen capsules can be used regardless of the particular pipetter utilized to process specimens.

Figure 35:
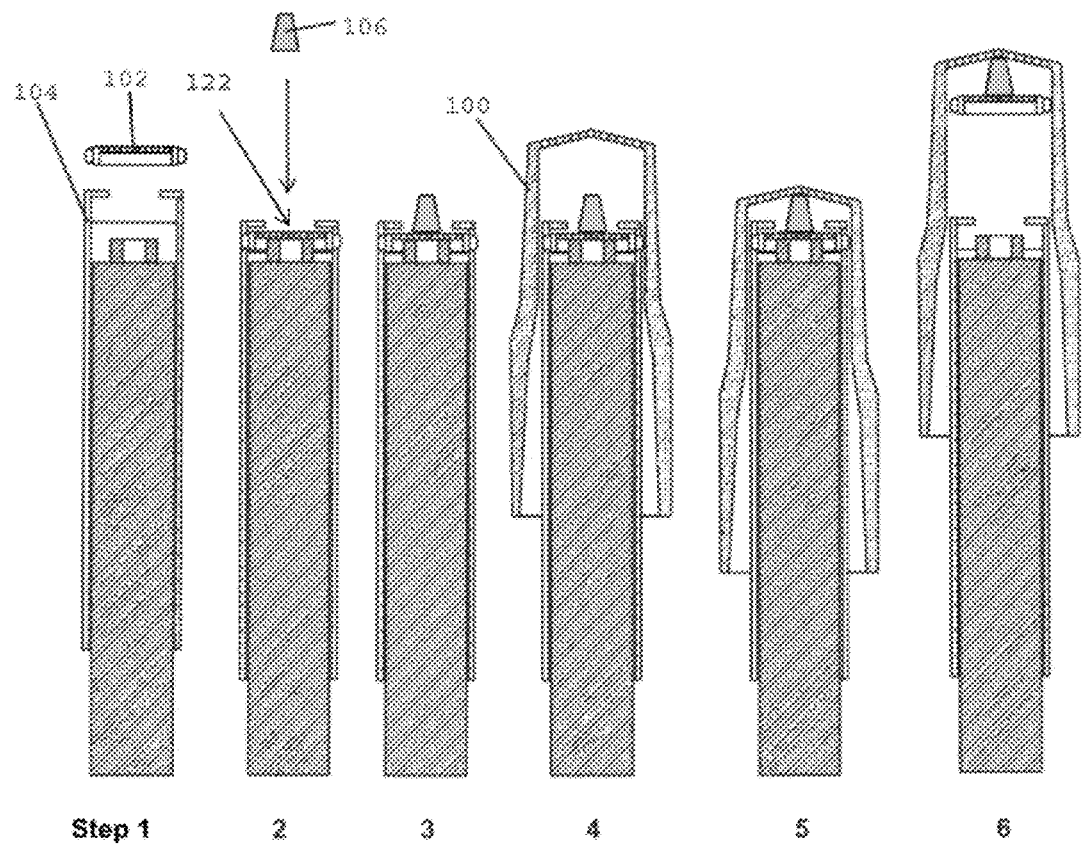

FIGS. 34 to 36 illustrate another aspect of one embodiment of the present disclosure that shows that inserts may be optimized for holding specimens of different sizes and shapes in preparation for study. Insert 102 includes web 122 with slit 144 but rod shaped specimen 360 may have a diameter that is too large to permit the pinching function to hold the specimen in place in the reservoir. It is anticipated that web 122 if insert 102 may be made of an easily cut or modified material permitting a user to excise portions of the web to accommodate large or oddly shaped specimens. In FIG. 35, the user has cut away a portion of the center of the web to create an opening 362 sized to fit the specimen 360. FIG. 36 illustrates specimen 360 within openings 362 created to accommodate the specimen.

Referring now to FIG. 37, an insert 102 may be used to hold and retain specimen 406 outside of a capsule. For this type of use, specimen 406 may be processed as described above by being retained by insert 102 and positioned within capsule 100 to permit processing of the sample. For this type of use, a resin may not be used to embed the sample but other steps such as fixation, dehydration and removal of any dehydrating chemicals may be taken to prepare the specimen for analysis and viewing. Specimen 406 and insert 102 can then be removed from the capsule. Insert 102 can then be positioned atop an imaging base 370 and held in place by some suitable adhesive 372 or otherwise attached to a base 370. This sort of mounting is useful for SEM microscopy.

The following are examples of use of the devices described above:

Example 1

Drop in Specimen Processing

This method of use is shown in FIG. 5. FIGS. 22 to 24 further show that the method shown in FIG. 5 can be used with specimens of various shapes are sizes are accommodated. It should be noted that insert 102 may be flipped over for handling larger specimens.

FIGS. 22 to 24 also show that the fluid level used for processing can be just enough to cover the specimen for almost all fluid steps. What is shown is the level of fluid D required for processing steps can be adjusted for the specimen size within the capsule, rather than requiring that the entire capsule be filled with fluids during processing. The more efficient use of fluids does not generally apply to the final resin that is used for preparing the TEM block where it is usually desired to fully fill the SHMP with resin, after placing the SHMP in a holder that seals the bottom of the capsules. It is widely understood and taught that fluid amounts equally only approximately 7-10 times the volume of the specimen are required for each fluid exchange. This more precise usage of fluids is achieved with the capsule, since most TEM specimens are less than 1×1×1 mm in size, equal to 1 ul or less in volume. The SHMP in one embodiment provides for over 100 ul of fluid. An additional feature that reduces the volume of solution is that the SHMP and insert may be used to place the specimen at or near the very end of the capsule. This placement of the specimen also reduces the amount of cutting that is required of the embedded specimen in order to begin sectioning.

Example 2

Orientation of Specimens by Placing the Specimens on Top of Insert

This method is shown in FIG. 25 and described above. FIGS. 10 to 16 show insert 102 in detail while FIGS. 17 to 21 illustrate the insertion tool 104 that are utilized in this method. FIGS. 19 to 21 shows the insert held in the insertion tool.

Example 3

Orientation of Specimens by Pinching the Back of the Specimens on Top of Insert

FIG. 26 shows this method of use. FIG. 16 shows how slit 144 of insert 102 can open by deflection of web 122. Slit 144 is also shown in various positions in other drawings herein with and without specimens inserted and held with the slit. FIGS. 17 to 21 shows the insertion tool 104 used in this method. For this method of use, both the inner and outer portions of tool 104 are used to hold the insert and deflect the web of the insert. FIGS. 19 to 21 show the assembly of inner and outer portion of tool 104 with the insert. FIGS. 34 to 36 show that the web of the insert can be readily cut or modified by users to obtain proper clamping of different shaped specimens.

It should be noted that since the specimen area that is sectioned is at the bottom of the SHMP capsule, it is usually acceptable to pinch the back or upper end of the specimen since this part of the specimen is not sectioned or imaged. Because of this, very long specimens can be accommodated, as shown in FIG. 27. An additional feature is that this can be used to place the region for examination of the specimen at or near the very end of the capsule. This placemen reduces the amount of cutting that is required of the embedded specimen in order to begin sectioning, thus saving time and effort.

Example 4

A Platform Apparatus for Holding the Insertion and Spreading Tools

FIG. 28 shows a simple apparatus for holding the insertion tool and the spreading tool for mounting specimens. As shown, the spreading tool is mounted on a firm and stable base and the insertion tool simply slides over it. This apparatus can be placed under a dissecting microscope or magnifying lens to enable viewing and manipulation of the specimen.

This configuration enables two fingers of one hand to control the pressure on the insert to open or close the insert to enable the placement of a specimen in the slit that is opened by the spreading tool. Once the specimen is properly placed in the insert, an SHMP capsule is slid over the fixture until the end of the specimen is at the end of the SHMP. The SHMP is rotated with the fingers of one hand to unlock the insert from the insertion tool, while two fingers of another hand are used to keep the insertion tool in place. The SHMP capsule with the placed specimen is then removed for processing by sliding upwards.

The method shown for mounting specimens without pinching, such as with adhesive or simple placement of a specimen on the SHMP insert, can also be performed on this platform apparatus. One simply does not provide pressure on the insertion tool to cause the spreader to press hard on the SHMP insert.

Example 5

A Platform and Lever Apparatus for Holding the Insertion and Spreading Tools

FIG. 29 shows a lever-activated system for engaging the spreading function. A clamp holds the insertion tool. A lever is provided which moves the spreading tool up or down as needed to deflect the web of the insert. This lever system may provide an upper processing platform 191 to provide provides a location for holding specimens prior to mounting. The top of the insertion tool is just above the platform 191 so that it is easy to manipulate and reach the SHMP insert, and it places the SHMP insert at very near the same level of focus as the platform 195 so that both are in focus when a dissecting microscope is used. A gap around the insertion tool mechanism may be large enough to slide an SHMP capsule over the insert to enable loading the capsule.

The method shown for mounting specimens without pinching, such as with adhesive or simple placement of a specimen on the SHMP insert, can also be performed on this platform and lever apparatus. One simply does not provide pressure on the lever to cause the spreader to press on the SHMP insert.

Example 6

A Platform and Lever Apparatus Workstation for Processing Specimens

FIG. 30 illustrates how the lever system of FIG. 29 may be incorporated into a workstation for efficient mass preparation of inserts, specimens and capsules for processing. The workstation may provide a highly-useful tool for orienting and inserting numerous specimens into capsules. The workstation enables users to work efficiently to establish precise specimen orientation. Adjustable feet accommodate its height to work with most dissecting scopes or viewers. Its clean layout enhances workflow and keeps supplies close-at-hand. This workstation may provide but is not limited to the following advantages:

Insertion tool at center positions insert for easy viewing during specimen orientation and insertion into capsule.
Entire specimen work area is easily viewed and lies in the same focal plane for manipulation of specimens and capsules.
Lever mechanism opens/closes the "pinch" action of mPrep/s capsules for establishing specimen orientation.
Specimen wells hold samples in 12 or more indexed depressions. Specimens may be prepared and stored in the wells until mounting, while keeping them from drying out. Sloped sides of the wells provide for easy clean out and prevent specimens from being trapped in corners.
Unfilled capsules & inserts may be stored along the top edge, readily accessible to the user.
Finished work storage may be provided on both ends of the Workstation. Rows of holes may be on standard spacing for multi-channel pipetters.

Work surface of chemically resistant and non-contaminating polyethylene, or similar material, is easy to clean and helps maintain sample purity.

Rounded front edge provides a comfortable hand rest.

Platform is designed to work with almost any stereomicroscope.

Lay out enhances workflow to maximize efficiency & prevent errors.

Example 7

Processing Multiple Specimens in Multiple SHMP Capsules on One Pipetter Shaft FIGS. 31 to 33 show how several SHMP capsules can be stacked on a single pipette to increase processing throughput. A limiting factor to the number of SHMP capsules is the volume of the pipetter. Conventional pipetters have a volume that generally limit this process to 3 capsules. As larger volume pipetter as provided, a larger number of capsules may be processed in this manner. Multi-channel pipetters can be used to process even more SHMP capsules simultaneously.

Additionally, the capsule most proximal to the pipetter can be fitted with a filter, to provide protection to the pipette mechanism by filtering out any solvents, resins or other materials and preventing them from entering the pipette mechanism. This can be a "regular" SHMP capsule or may be a specialized version, such as a version with larger holes.

As noted above, an adapter capsule may be used in the processing of multiple capsules with pipetters that conform to a different standard than the SHMP capsules. Such an adapter capsule will permit SHMP capsules to be used with almost any pipetter.

Example 8

Custom Modification of SHMP Insert

FIGS. 34 to 36 illustrate how an insert can be cut by the end user to enable the insert to accommodate specimens of different sizes or shapes. For example, a botanist may wish to mount portions of roots or leaves in specific orientations, and may often work with specimens of the same or different size but that are too thick for the tight pinching action of the SHMP insert slit. Similarly, a mammalian physiologist may wish to mount nerve bundles, or retina, or muscle slices, or other tissues for imaging and analysis. And similarly, a material scientist may have other materials with a size or shape that can be readily accommodated by cutting or otherwise modifying the insert.

Example 15

Using SHMP Inserts to Hold Specimens for SEM

Tissue specimens or other types of specimens can be processed within a capsule for SEM viewing and analysis and then removed from the capsule to be held vertically with the SHMP inserts to enable viewing with SEM, while enabling the small reagent volumes of the SHMP processing. Moreover, the SHMP capsule provides protection of the specimen during processing with fixatives, solvents, and the like, and while being processing by drying with the critical point method, and by other preparation methods.

Example 16

A Silicone Holder to Hold SHMP Capsules During Certain Processing Steps

Figure 38:
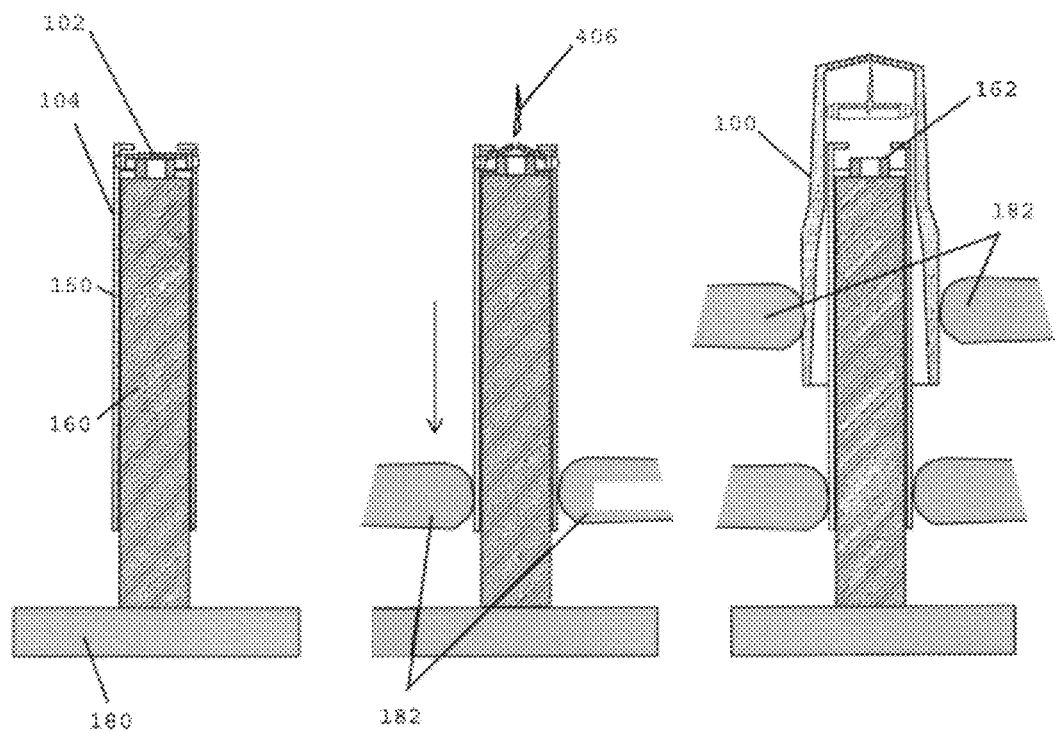
FIG. 38 is an image of a portion of a rack for holding a plurality of capsules according to the present disclosure and sealing a second open end of the capsule to permit a plurality of capsules to be processed at the same time.
Figure 41:
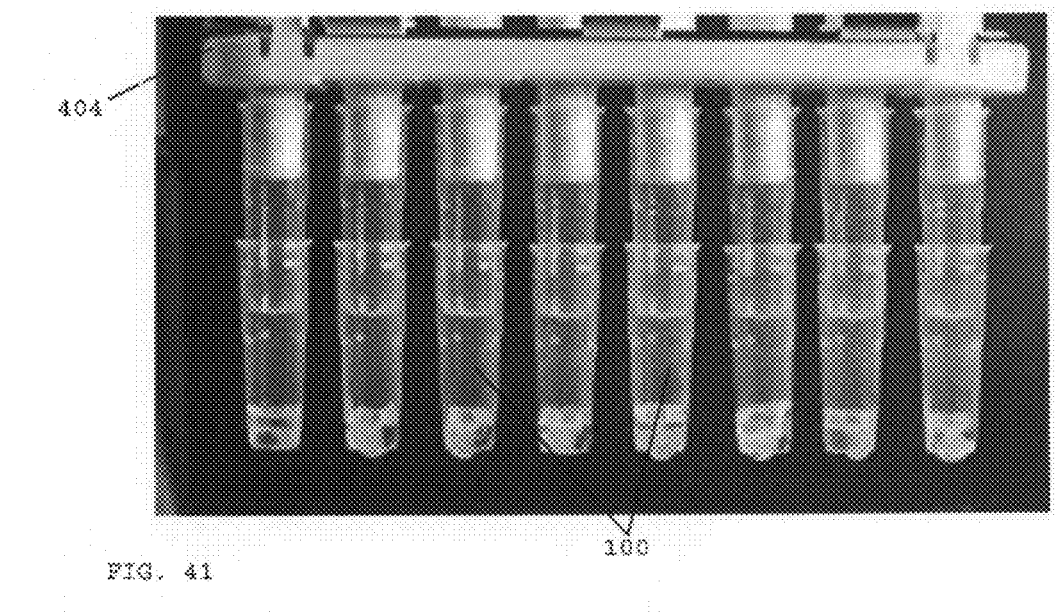
FIG. 41 is an image of a plurality of capsules according to the present disclosure mounted to a multiple tip pipetter for simultaneous processing of specimens within the capsules.

FIG. 38 illustrates a tray or holder 400 with a base 401 into which may be formed a plurality of recesses 402 for receiving capsules 100 or other pipette tips that have been removed from a pipetter. The recesses may be arranged and spaced apart so that the capsules are positioned to be engaged by a multiple pipette device 404 such as shown in FIG. 41. Holder 400 may also permit capsules 100 to be sealed at the lower or second end to permit polymerization of resin within the capsule to prepare the capsule and specimen for sectioning. It is also anticipated capsules held within holder 400 may be exposed to other fluids requiring a longer dwell time during processing. Holder 400 is preferably a unique rack made of a silicone elastomer or other suitable sealing elastomer or other sealing material for holding capsules. A resilient deformable material would preferably be used to construct holder 400 so that insertion of capsules or other pipette tips within recesses 402 will deflect the material to form a seal about the capsule or pipette tip and close off an open bottom of the capsule or pipette tip. It may also be used with the present disclosure to retain fluid within capsules during various stages of processing such as for microwave processing.

Non-limiting examples of how holder 400 may be used to enhance specimen processing include:
1. Holding filled SHMP capsules for long treatment protocols.
2. Polymerizing embedding resins in a conventional oven.
3. Microwave processing of specimens or TEM grids.
4. Culturing cells or tissues adherent to tissue growing scaffolds or surfaces held within SHMP capsules.
5. Convenient bench-top holder for SHMP capsules.

Some desired or preferred characteristics of holder 400 may include but are not limited to:
Durable high quality silicone construction
Microwave compatible
Oven safe to greater than 100° C.
Indexed positions of recesses.
Sterilize with steam, autoclave or boiling water
SBS standard shape, size and spacing to make this rack suitable for laboratory robotics systems and devices.

Figure 39:
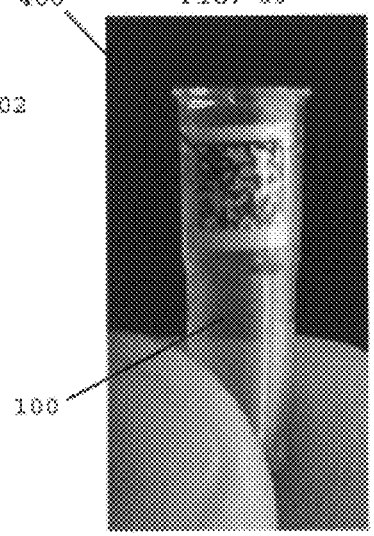
FIG. 39 is an image of a capsule according to the present disclosure that is filled with the embedding plastic that was cured with the capsule held in the block described in FIG. 38. This including an indicia as part of the capsule for tracking the capsule and any specimen that might be contained within the capsule.

FIG. 39 illustrates that a label 408 may be inserted into capsule 100 prior to polymerization for permanent labeling of the fully processing specimen.

Example 17

Reduced Cutting and Trimming Prior to Sectioning

Figure 40:
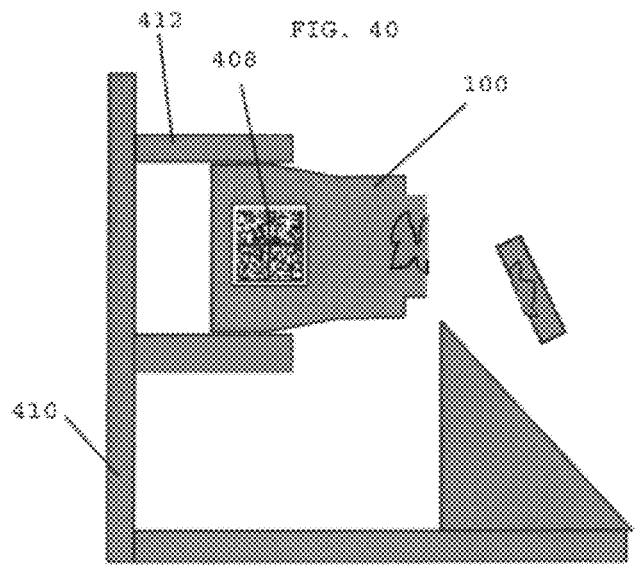
FIG. 40 is a side diagrammatic view of a capsule according to the present disclosure positioned within a microtome for sectioning.

FIG. 40 shows that embedded specimens within SHMP capsules can be directly mounted into a microtome chuck 412 of a microtome 410 without removing the resin from the capsule. This saves time by eliminating the need to remove the hard resin from the embedding capsule. Of course, the embedded specimen block can also be removed from the SHMP capsule if desired, but cutting away the capsule as is current common practice.

Example 18

Using SHMP Capsules for Tissue Culture

FIG. 41 shows that capsules 100 can be used to hold tissues for tissue culture, or other applications such as for tissue and biochemical assays. This has all the advantages of low reagent consumption as used for TEM or SEM specimen preparation. This also uses the displacment pipette fluid deliver systems, therefore facilitating the operation of biochemical assays. Clear vessels enable viewing of the specimens within the capsule.

The present disclosure enables orientation of a specimen such as fresh tissue, or at almost any other time. Thus tissue samples can be partially processed such as through but not limited to fixation, stained if desired to facilitate seeing particular features, and then removed from the capsule, orientated, and then reinserted into the capsule to complete processing.

The present disclosure enables processing of small tissue specimens, or larger tissue specimens, and enables the processing with only the precise amount of processing chemicals needed to be used since small specimens may be positioned in the bottom of SHMP capsule. The capsule then only needs to be filled to the height of the specimen so that no more chemicals are used than are necessary for a particular specimen.

The present disclosure further enables the positioning and processing of specimens in such a way that does not require that specimens be oriented.

The present disclosure provides two different methods for obtaining orientation, 1—Pinching the specimen within a slit or other opening within the insert, 2—balancing the specimen on the insert, gluing or otherwise affixing the specimen to the insert.

The present disclosure describes a capsule or single vessel that provides several functions:
  A vessel used to hold the specimens during processing. This is analogous to vials/jars that are commonly used to process specimens manually.
  Serves as part of a fluid delivery system for processing by engaging onto a laboratory pipetter or other similar fluid delivery device. This is analogous to the common practice of filling and emptying vials/jars using Pasteur pipettes as are commonly used to process specimens manually.
  A porous capsule to hold specimens during processing by immersion—analogous to histocassettes. However the present invention can also be used in immersion processers as well as critical point dryers.
  A capsule that may used to polymerize the resin used in TEM—acting like the embedding capsules used for non-orientated specimen embedding.
  A capsule that is provides for a function like that of the standard flat embedding molds used to polymerize the resin used in TEM—by providing a means to enable the orientation of the specimen in the "block."

The present disclosure further describes an insert for use with the capsule above that performs but is not limited to performing the following several functions:
  Insert may be easily removed at any time up to resin polymerization for orientation of tissue, or re-orientation.
  Insert entraps the specimen in the capsule into the bottom of the capsule, or other desired location. By placing the insert as close to the bottom of the capsule as the particular specimen allows, the placement may reduce the amount of chemical used to process the specimen.
  By securing the specimen as near as possible to the bottom of the capsule, minimal cutting of the capsule after processing the specimen is necessary to begin sectioning the actual specimen.
  Insert may be used to clamp or pinch some specimens in the proper orientation.
  Specimens may be glued or otherwise affixed to the insert to provide for easy orientation.
  Insert is fully accessible for placing specimens when held in the Insertion Tool.
  Insert may be used outside of a capsule to support specimens upright for SEM, or other applications or instruments.

The present disclosure also describes an insertion tool for use with the insert and capsule described above.
  Insertion tool can be used with the capsules facing up or down—used for handling different types of specimens.
  A workstation may incorporate an insertion tool that facilitates obtaining proper orientation of specimens in a compact and efficient workspace.
  Insertion tools and spreading tools may be used with base or workstation to facilitate handling of specimens, inserts and capsules.
  Insertion tools and spreading tools may also be used without base of workstation.
  Workstation that provides an integrated platform for high throughput processing of specimens.

The present disclosure further relates to but is not limited to the following applications:
  TEM specimen preparation
  SEM specimen preparation
  LM specimen preparation
  Preparation of tissue culture or organ culture specimens for examination and evaluation.

Therefore, in one method of use, the invention provides a device for preparing microscopy specimens in which the specimens are easily introduced into the specimen preparation capsule. The specimen preparation capsule has been referred to as the SHMP in earlier US patent applications and patents commonly owned by the present applicant. The present disclosure enables an improved method and device for to trapping a specimen within the SHMP where it remains throughout all processing including fixation, dehydration, and embedding in resin by virtue of but not limited to displacement pipetting method and other fluid silvery methods disclosed in prior US patent applications and patents commonly owned by the present applicant. Further, a SHMP capsule that has been filled with an embedding resin can be directly mounted into many microtome chucks for sectioning, thus eliminating the need to remove the resin block containing the fully processed specimen from the molding capsule.

Therefore, in one embodiment the present disclosure provides a device or capsule for preparing microscopy specimens comprising a reservoir. In this embodiment, the reservoir may have a first end adapted and configured to accept a pipette and a second end having an aperture therein. Further included may be a replaceable cap for the first and second ends such that when the caps are placed on the first end and the second end, the specimen is sealed inside. In this embodiment, a first end of a first capsule may be dimensioned and configured to accept a second end of a second capsule such that the second end of the second capsule is received within the reservoir of the first capsule. This may permit a plurality of the capsules to be stacked one on top of each other. In addition, in some preferred embodiments, the reservoir of the capsule may be adapted to contain a specimen for microscopic evaluation and displacement of the pipette results in filling or emptying of the reservoir. In this fashion filling of the reservoir with desired reagent prepares the sample for microscopy.

In yet another embodiment, the present disclosure provides a device such as a capsule for preparing specimens for microscopic analysis, the capsule comprising one or more of the following features: a reservoir; the reservoir having a first end adapted to accept a pipette and a second end having an aperture; the aperture including a screen; an indicia; a cap for the first end; and a cap for the second end. According to this embodiment, the first end of the first capsule may be designed and configured to accept the second end of a second capsule. In use, the displacement of a pipette attached to the first end of the reservoir allows for the filling and emptying of one or more fluids in the reservoir such that a specimen held in the reservoir is fixed for microscopic analysis.

In yet another embodiment the present disclosure provides a method for preparing specimens for microscopic analysis comprising placing one or more specimens in a reservoir, connecting a displacement device to a first end of the reservoir and passing fixation fluids through the reservoir via displacement of the displacement device such that on completion the specimen has been prepared for microscopic analysis entirely within the reservoir.

These and other features of various exemplary embodiments of the methods according to this invention are described in, or are apparent from, the following detailed description of various exemplary embodiments of the methods according to this invention.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A system for preparing and holding specimens for microscopic analysis, cells, tissue culture or organ culture, the system comprising:
    a capsule having a first open end, a second end including at least one aperture, and defining a reservoir between the first open end and the second end, the reservoir having an inner wall defining an inner wall upper portion adjacent the first open end of the capsule and an inner wall lower portion adjacent the second end of the capsule, wherein the inner wall is wider adjacent the first open end in the upper portion and narrower adjacent the second end in the lower portion, and wherein the sides of the inner wall in the lower portion are generally parallel to each other; and
    a removable insert with a circumferential base and including a web extending across its center and including at least one aperture extending therethrough, the base configured to fit through the upper portion of the inner wall of the reservoir and to adjustably engage the inner wall of the reservoir in the lower portion so that a friction fit between the base and the inner wall will secure the insert in position within the reservoir, wherein the position of the insert in the lower portion of the reservoir defines a sample holding region between the insert and the second end of the capsule;
    an insertion tool configured to be inserted into the open end of the capsule and to releasably engage tabs on the insert with a plurality of arms at an insert engaging end of the insertion tool so that a portion of the insert extends beyond an outer surface of the insertion tool, the insertion tool sized to fit within the reservoir and position the insert within the lower portion of the reservoir, the insertion tool configured to permit the positioning of the insert at one or more positions within the reservoir, the insertion tool further configured to disengage the insert once the insert is positioned within the inner wall of the reservoir.

2. The system of claim 1, wherein the apertures of the second end of capsule and the apertures of the insert are 200-300 μm in diameter.

3. The system of claim 1, wherein the circumferential base of the insert comprises a plurality of tabs, the tabs sized to engage the inner wall of the reservoir within the lower portion, while retaining specimen in the lower portion.

4. The system of claim 1, wherein the web of the insert further includes a transverse slit across a portion of the web, wherein the insert is made of a resilient deformable material such that deflection of the web will cause the transverse slit to open to permit the mounting of a specimen to the insert.

5. The system of claim 1,
    wherein the web of the insert further includes a transverse slit across a portion of the web, wherein the insert is made of a resilient deformable material such that deflection of the web will cause the transverse slit to open to permit the mounting of a specimen to the insert, and
    wherein the insertion tool includes an inner spreading portion slidably received within an outer portion of the insertion tool, the inner spreading portion having a spreading tip configured to contact an insert held by the insert engaging end of the insertion tool and to deflect the web of the insert to open the transverse slit and permit the mounting of the specimen to the insert.

6. The system of claim 1, wherein the insertion tool is releasable from the insert within the reservoir by rotation of the insertion tool relative to the insert.

7. The system of claim 1, wherein the insertion tool is mounted in a specimen processing surface, wherein the insert engaging end extends through the specimen processing surface so that an insert held by the insert engaging end is accessible at the specimen processing surface.

8. The system of claim 7,
    wherein the web of the insert further includes a transverse slit across a portion of the web, wherein the insert is made of a resilient deformable material such that deflection of the web will cause the transverse slit to open to permit the mounting of a specimen to the insert,
    wherein the insertion tool includes an inner spreading portion slidably received within an outer portion of the insertion tool, the inner portion having a spreading tip configured to contact an insert held by the insert engaging end of the insertion tool and to deflect the web of the insert to open the transverse slit and permit the mounting of the specimen to the insert; and
    wherein the insertion tool further comprises a lever with a first end accessible to a user of the system and a second end in communication with the inner portion of the insertion tool, so that a user may move the first end of the lever to bring the spreading tip of the inner portion into contact with the web and open the transverse slit of the insert to mount a specimen to the insert.

9. The system of claim 1, wherein the bottom of the reservoir is wedged, tapered or curved to facilitate centering of a specimen within the reservoir and adjacent to the at least one aperture.

10. The system of claim 1, wherein the capsule is a first capsule and further comprising a second capsule with a first end and a second end, the second end of the second capsule configured to be positioned within the first end of the first capsule, the first end of the second capsule configured to engage a pipette tip for delivering fluid to and evacuating fluid from the reservoir of the first capsule.

11. The system of claim 10, the second capsule further comprising a filter within a reservoir of the second capsule.

12. The system of claim 1, wherein the apertures of the second end of capsule and the apertures of the insert are 5-10 μm in diameter.

13. The system of claim 4, wherein the insert has a flat bottom to provide a stable supporting and mounting platform to enable the sample to be held vertically outside of a capsule for analysis or viewing.

\* \* \* \* \*